US010928339B2

(12) United States Patent
Maekawa et al.

(10) Patent No.: US 10,928,339 B2
(45) Date of Patent: Feb. 23, 2021

(54) CATALYTIC-CONVERSION-TYPE SENSOR

(71) Applicant: NEW COSMOS ELECTRIC CO., LTD., Osaka (JP)

(72) Inventors: Toru Maekawa, Osaka (JP); Chise Minagoshi, Osaka (JP); Kenji Ishibashi, Osaka (JP); Hiroshi Miyazaki, Osaka (JP)

(73) Assignee: NEW COSMOS ELECTRIC CO., LTD., Osaka (JP)

( * ) Notice: Subject to any disclaimer, the term of this patent is extended or adjusted under 35 U.S.C. 154(b) by 97 days.

(21) Appl. No.: 15/775,701

(22) PCT Filed: Nov. 14, 2016

(86) PCT No.: PCT/JP2016/083735
§ 371 (c)(1),
(2) Date: May 11, 2018

(87) PCT Pub. No.: WO2017/082431
PCT Pub. Date: May 18, 2017

(65) Prior Publication Data
US 2018/0328873 A1  Nov. 15, 2018

(30) Foreign Application Priority Data

Nov. 13, 2015  (JP) .............................. JP2015-223022
Nov. 14, 2016  (JP) .............................. JP2016-221959
Nov. 14, 2016  (JP) .............................. JP2016-221960

(51) Int. Cl.
*G01N 25/00* (2006.01)
*G01N 31/10* (2006.01)
(Continued)

(52) U.S. Cl.
CPC ........... *G01N 25/30* (2013.01); *G01N 31/005* (2013.01); *G01N 33/0013* (2013.01);
(Continued)

(58) Field of Classification Search
CPC ............... G01N 25/30; G01N 33/0037; G01N 33/0052; G01N 31/005; G01N 33/0013; G01N 31/10
See application file for complete search history.

(56) References Cited

U.S. PATENT DOCUMENTS 5,879,525 A  3/1999  Kato
2005/0061667 A1*  3/2005  Suzuki ............... G01N 33/0037
204/401

(Continued)

FOREIGN PATENT DOCUMENTS

CN  102914575 A  2/2013
JP  7128280 A  5/1995
(Continued)

*Primary Examiner* — Benjamin R Whatley
*Assistant Examiner* — Jean Caraballo-Leon
(74) *Attorney, Agent, or Firm* — Innovation Capital Law Group, LLP; Vic Lin

(57) ABSTRACT

The present invention provides a catalytic conversion-type sensor that detects a detection target gas by detecting a conversion gas produced through a reaction, the catalytic conversion-type sensor including: a gas flow path that allows the detection target gas to flow down; and a conversion portion that is connected to the gas flow path, the conversion portion including, on a side partitioned by a diffusion means that allows the detection target gas to naturally diffuse, a heated catalyst portion that produces a conversion gas by causing the detection target gas to come into contact with a heated catalyst and react with the heated catalyst, and a sensor element portion that is capable of detecting the conversion gas produced through the reaction.

14 Claims, 13 Drawing Sheets

(51) Int. Cl.
  *G01N 21/00*  (2006.01)
  *G01N 33/00*  (2006.01)
  *G01N 25/30*  (2006.01)
  *G01N 31/00*  (2006.01)

(52) U.S. Cl.
  CPC ..... *G01N 33/0037* (2013.01); *G01N 33/0052* (2013.01); *G01N 31/10* (2013.01)

(56) References Cited

U.S. PATENT DOCUMENTS

| | | | |
|---|---|---|---|
| 2006/0133962 A1* | 6/2006 | Otani | G01N 27/16 422/94 |
| 2007/0131567 A1 | 6/2007 | Park et al. | |
| 2011/0113855 A1* | 5/2011 | Badding | G01N 29/022 73/24.06 |
| 2012/0273846 A1* | 11/2012 | Neff | G01N 27/4141 257/253 |

FOREIGN PATENT DOCUMENTS

| | | |
|---|---|---|
| JP | 08170954 A | 7/1996 |
| JP | 8247995 | 9/1996 |
| JP | 200222725 A | 1/2002 |
| JP | 2003075342 A | 3/2003 |
| JP | 2009092431 A | 4/2009 |
| JP | 2009518647 A | 5/2009 |
| JP | 2014199231 A | 10/2014 |
| WO | 2005015191 A1 | 2/2005 |

\* cited by examiner

CATALYTIC-CONVERSION-TYPE SENSOR

TECHNICAL FIELD

The present invention relates to a catalytic conversion-type sensor that detects a detection target gas by detecting a conversion gas produced through a reaction. The reaction may be an oxidation reaction or a thermal decomposition reaction.

BACKGROUND ART

In general, fluorine-based special gases such as nitrogen trifluoride ($NF_3$), $C_4F_6$, $C_4F_8$, and carbon tetrafluoride that are used as etching gases or cleaning gases in semiconductor manufacturing are considered to impose a load on the surrounding environment. Accordingly, measures are taken so that a fluorine-based special gas such as nitrogen trifluoride is not released (does not escape) to the surrounding environment by detecting the leakage of a fluorine-based special gas.

It is known that gas sensors have low sensitivity to such fluorine-based special gases because fluorine-based special gases cannot be detected directly through an electrochemical reaction, and thus fluorine-based special gases are converted to another gas through thermal decomposition in advance so as to be detectable by sensors.

For example, nitrogen trifluoride can be detected by converting it to nitrogen dioxide ($NO_2$) through thermal decomposition in advance.

The above-described technique for "detecting a detection target gas by detecting a conversion gas produced through thermal decomposition", which is defined as a conventional technique in the present invention, is a commonly known technique, and thus conventional technical documents such as patent documents are not listed here.

DISCLOSURE OF THE INVENTION

Problem to be Solved by the Invention

However, the rate of conversion (conversion rate) of nitrogen trifluoride to nitrogen dioxide is as low as about a few % (about 3%), and thus it has been difficult to efficiently detect nitrogen trifluoride. Also, the conversion rate is dependent on the flow rate. Accordingly, there is a possibility that if the flow rate per unit time increases due to degradation of the flow rate sensor, the conversion rate will further decrease. Furthermore, in order to detect nitrogen trifluoride, it is necessary to additionally provide a thermal decomposition unit, which tends to lead to an increase in the size of the apparatus.

Also, in order to produce a conversion gas by thermally decomposing another fluorine-based special gas, it is necessary to heat the fluorine-based special gas, which normally requires the use of a thermal decomposition furnace that includes a large heat source and a thermal insulation mechanism. This also tends to lead to an increase in the size of the apparatus.

Accordingly, it is an object of the present invention to provide a catalytic conversion-type sensor that can improve the conversion rate, and achieve miniaturization.

Means for Solving Problem

A first characteristic configuration of a catalytic conversion-type sensor according to the present invention for achieving the above-described object is that the catalytic conversion-type sensor that detects a detection target gas by detecting a conversion gas produced through a reaction, the catalytic conversion-type sensor includes: a gas flow path that allows the detection target gas to flow down; and a conversion portion that is connected to the gas flow path, the conversion portion including, on a side partitioned by a diffusion means that allows the detection target gas to naturally diffuse, a heated catalyst portion that produces a conversion gas by causing the detection target gas to come into contact with a heated catalyst and react with the heated catalyst, and a sensor element portion that is capable of detecting the conversion gas produced through the reaction.

With the catalytic conversion-type sensor configured as described above, because the diffusion means allows the detection target gas flowing down through the gas flow path to naturally diffuse toward the conversion portion, the amount of detection target gas that migrates to the conversion portion can be made less dependent on the flow amount of gas that flows down through the gas flow path. For this reason, even if the flow rate of the detection target gas flowing down through the gas flow path varies over time due to degradation of the flow rate sensor, it does not directly affect the amount of the detection target gas that migrates to the conversion portion, and thus the amount of detection target gas that migrates to the conversion portion is unlikely to vary. Accordingly, with the catalytic conversion-type sensor according to the present invention, the conversion rate for converting the detection target gas to the conversion gas is unlikely to be affected by the flow rate of the detection target gas, and thus the conversion rate is unlikely to decrease over time.

Also, with the diffusion means configured as described above, the detection target gas that naturally diffuses into and stays in the conversion portion can be efficiently brought into contact with the heated catalyst portion, and thus the conversion rate can be improved.

Also, with the catalytic conversion-type sensor according to the present invention, the conversion portion includes the heated catalyst portion and the sensor element portion, and thus it is unnecessary to additionally provide a thermal decomposition unit or use a large thermal decomposition furnace, as a result of which miniaturization can be achieved.

A second characteristic configuration of the catalytic conversion-type sensor according to the present invention is that the diffusion means has an air resistance of 800 $mm \cdot Pa^{-1} \cdot s^{-1}$ or less.

This configuration allows at least a portion of the detection target gas flowing down through the gas flow path to pass through the pores of the diffusion means and into the conversion portion in a state in which it is unlikely to be influenced by the flow pressure of the detection target gas.

A third characteristic configuration of the catalytic conversion-type sensor according to the present invention is that the diffusion means includes a resin film with a hole portion having a predetermined hole diameter and a gas permeable porous film that are adjacently provided.

With this configuration, by forming the hole portion in the resin film, it is possible to adjust the amount of detection target gas that permeates through the diffusion means and naturally diffuses into the conversion portion. Also, the gas permeable porous film can be configured to have a desired porosity for the detection target gas to naturally diffuse into the conversion portion.

The diffusion means is configured to transmit the detection target gas such that the detection target gas flowing down through the gas flow path can naturally diffuse toward the conversion portion, but it is desirable to configure the diffusion means such that the conversion gas produced in the conversion portion does not easily permeate through the diffusion means and migrate toward the gas flow path. That is, if the conversion gas cannot easily migrate toward the gas flow path, the conversion gas can be efficiently detected by the sensor element portion. For this reason, with the diffusion means as described above configured to include the resin film and the porous film that are adjacently provided, by variously setting the hole diameter of the hole portion, and the like, and also variously changing the air permeability of the porous film, it is possible to specify the air resistance of the diffusion means such that the detection target gas used can naturally diffuse toward the conversion portion, and the conversion gas cannot easily migrate from the conversion portion toward the gas flow path.

A fourth characteristic configuration of the catalytic conversion-type sensor according to the present invention is that the diffusion means is a resin film with a hole portion having a predetermined hole diameter.

With this configuration, it is possible to adjust the amount of detection target gas that permeates through the diffusion means and naturally diffuses into the conversion portion, with the use of a simple configuration.

A fifth characteristic configuration of the catalytic conversion-type sensor according to the present invention is that the reaction is oxidation.

With this configuration, the conversion gas can be produced as a result of the oxidation effect of the catalyst, rather than thermal decomposition of the detection target gas. Accordingly, the heating temperature of the heated catalyst portion can be suppressed.

A sixth characteristic configuration of the catalytic conversion-type sensor according to the present invention is that the detection target gas is nitrogen trifluoride, and the conversion gas is nitrogen dioxide.

With this configuration, it is possible to efficiently detect nitrogen trifluoride, to which the sensitivity of a gas sensor is low and that cannot be detected directly through an electrochemical reaction, by converting it to nitrogen dioxide.

A seventh characteristic configuration of the catalytic conversion-type sensor according to the present invention is that the catalyst in the heated catalyst portion is a noble metal catalyst that contains Pd and Pt, and the sensor element portion is an electrochemical nitrogen oxide sensor element that contains noble metal carrying carbon and is configured to be capable of detecting nitrogen dioxide.

With this configuration, such an electrochemical nitrogen oxide sensor element that contains noble metal carrying carbon and is configured to be capable of detecting nitrogen dioxide is highly sensitive to nitrogen dioxide, and can be miniaturized. Accordingly, with the catalytic conversion-type sensor configured as described above, it is possible to achieve further miniaturization of the catalytic conversion-type sensor.

An eighth characteristic configuration of the catalytic conversion-type sensor according to the present invention is that the heated catalyst portion is a contact combustion-type sensor, and a detection element included in the contact combustion-type sensor has a spherical diameter of 0.76 to 1.08 mm, the detection element including the catalyst and being configured to respond to the detection target gas.

With this configuration, it is possible to achieve a range in which the detection target gas can be oxidized and the conversion gas can be produced with excellent efficiency, and satisfies a preferred response rate (less than or equal to 60 seconds).

A ninth characteristic configuration of the catalytic conversion-type sensor according to the present invention is that the heated catalyst portion is heated to 300 to 700° C.

With this configuration, it is possible to achieve both a preferred response rate (less than or equal to 60 seconds) and detectable sensitivity.

A tenth characteristic configuration of the catalytic conversion-type sensor according to the present invention is that the heated catalyst portion has an applied voltage of 0.68 to 1.85 V.

With this configuration, the temperature of the detection element can be set to an appropriate temperature, and it is possible to achieve both a preferred response rate (less than or equal to 60 seconds) and detectable sensitivity.

An eleventh characteristic configuration of the catalytic conversion-type sensor according to the present invention is that the reaction is thermal decomposition.

With this configuration, the catalytic conversion-type sensor according to the present invention can be used not only in the case where the conversion gas is produced through an oxidation reaction, but also in the case where the conversion gas is produced through a thermal decomposition reaction.

A twelfth characteristic configuration of the catalytic conversion-type sensor according to the present invention is that the diffusion means includes at least a gas permeable porous film.

With this configuration, the gas permeable porous film can be configured to have a desired porosity for the detection target gas to naturally diffuse into the conversion portion.

A thirteenth characteristic configuration of the catalytic conversion-type sensor according to the present invention is that the detection target gas is hexafluoro-1,3-butadiene ($C_4F_6$), and the conversion gas is hydrogen fluoride.

With this configuration, it is possible to efficiently detect hexafluoro-1,3-butadiene, to which the sensitivity of a gas sensor is low and that cannot be detected directly through an electrochemical reaction, by converting it to hydrogen fluoride.

A fourteenth characteristic configuration of the catalytic conversion-type sensor according to the present invention is that the catalyst in the heated catalyst portion is a noble metal catalyst that contains Pd and Pt, and the sensor element portion is an electrochemical sensor element that contains noble metal carrying carbon and is configured to be capable of detecting hydrogen fluoride.

With this configuration, such an electrochemical sensor element that contains noble metal carrying carbon and is configured to be capable of detecting hydrogen fluoride is highly sensitive to hydrogen fluoride, and can be miniaturized. Accordingly, with the catalytic conversion-type sensor configured as described above, it is possible to achieve further miniaturization of the catalytic conversion-type sensor.

BEST MODE FOR CARRYING OUT THE INVENTION

Hereinafter, an embodiment of the present invention will be described with reference to the drawings.

Figure 1:
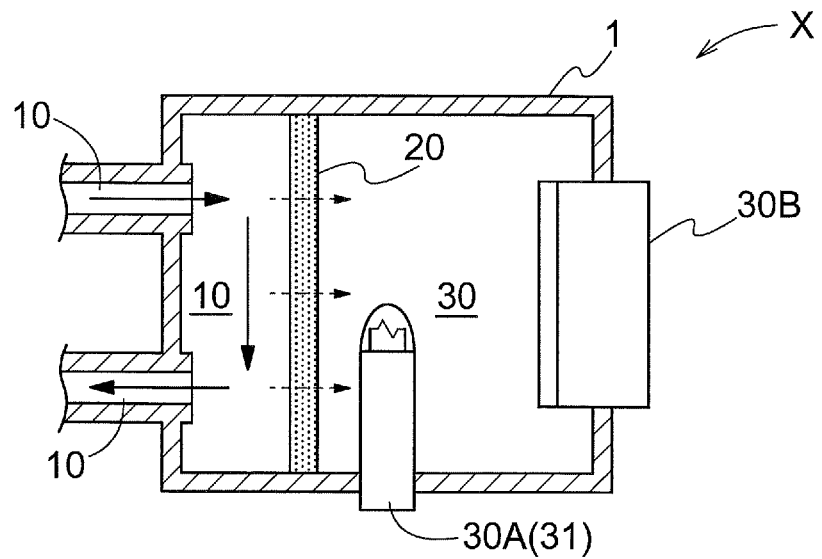
FIG. 1 is a schematic cross sectional view of a catalytic conversion-type sensor according to the present invention.

As shown in FIG. 1, a catalytic conversion-type sensor X according to the present invention includes: in order to detect a detection target gas by detecting a conversion gas produced through a reaction, a gas flow path 10 that allows the detection target gas to flow down; and a conversion portion 30 that is connected to the gas flow path 10, the conversion portion 30 including, on a side partitioned by a diffusion means 20 that allows the detection target gas to naturally diffuse, a heated catalyst portion 30A that produces a conversion gas by causing the detection target gas to come into contact with a heated catalyst 31 and react with the heated catalyst 31, and a sensor element portion 30B that is capable of detecting the conversion gas produced through the reaction.

In the present embodiment, an example will be described in which the reaction is an oxidation reaction, the detection target gas is nitrogen trifluoride, the conversion gas is nitrogen dioxide, and the sensor element portion 30B is an electrochemical nitrogen oxide sensor element that is capable of detecting nitrogen dioxide, but the present embodiment is not limited thereto. For example, in the case where the sensor element portion 30B is an electrochemical nitrogen oxide sensor element, it is possible to use ammonia as the detection target gas. Alternatively, in the case where the sensor element portion 30B is a sensor element that is capable of detecting carbon monoxide or carbon dioxide as the conversion gas, it is possible to use any other gas as the detection target.

The diffusion means 20 functions as a separator that separates the gas flow path 10 and the conversion portion 30 from each other. Accordingly, it is sufficient that the diffusion means 20 is configured such that the gas flow path 10 and the conversion portion 30 can be spatially distinguished from each other. The diffusion means 20 is configured to transmit the detection target gas such that the detection target gas flowing down through the gas flow path 10 can naturally diffuse toward the conversion portion 30. That is, a portion of the detection target gas flowing down through the gas flow path 10 directly flows down toward the downstream side of the gas flow path 10, and the remaining portion of the detection target gas permeates through the diffusion means 20 and naturally diffuses into the conversion portion 30. Here, the term "naturally diffuse" used in this specification refers to a state in which at least a portion of the detection target gas flowing down through the gas flow path 10 passes through the pores of the diffusion means 20 and permeates into the conversion portion 30 under in a state in which it is unlikely to be influenced by the flow pressure of the detection target gas, instead of forcibly causing the detection target gas to pass through the pores of the diffusion means 20 and permeate into the conversion portion 30 by, for example, pressurizing the detection target gas.

The diffusion means 20 as described above is configured to have an air resistance of 800 $mm \cdot Pa^{-1} \cdot s^{-1}$ or less, and preferably an air resistance of 50 to 800 $mm \cdot Pa^{-1} \cdot s^{-1}$.

The diffusion means 20 may be formed by combining different materials, or may be formed using a single material.

In the present embodiment, a case will be described where the diffusion means 20 is formed by combining different materials.

Figure 2:
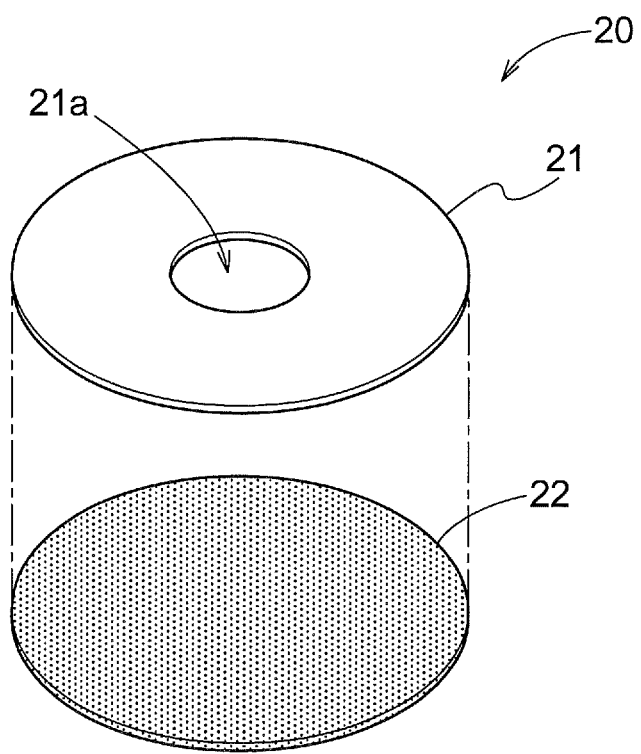
FIG. 2 is a schematic view of a diffusion means

In the case where the diffusion means 20 is formed by combining different materials, as shown in FIG. 2, the diffusion means 20 can be formed by adjacently providing and stacking together a resin film 21 that has a hole portion 21a having a predetermined hole diameter and a gas permeable porous film 22, but the configuration is not limited thereto. In the case of stacking the resin film 21 and the porous film 22 together, the resin film 21 and the porous film 22 may be provided such that the resin film 21 is provided on the side of the gas flow path 10, and the porous film 22 is provided on the side of the conversion portion 30.

The resin film 21 may be a thin film obtained by molding a polymer component such as a plastic synthetic resin, but the resin film 21 is not limited thereto. In the resin film 21, one or more hole portions 21a having a predetermined hole diameter are formed. The amount of detection target gas that permeates through the diffusion means 20 and naturally diffuses into the conversion portion 30 can be adjusted by setting the hole diameter of the hole portions 21a and the number of hole portions 21a. The amount of detection target gas may be adjusted by setting the hole diameter of the hole portions 21a and the number of hole portions 21a so as to attain a desired amount of detection target gas.

The porous film 22 may be a gas permeable porous film, or the like, but the porous film 22 is not limited thereto. Such a porous film may be, for example, a PTFE (polytetrafluoroethylene) film, or the like. The porous film 22 can be configured to have a desired porosity for the detection target gas to naturally diffuse into the conversion portion 30.

As described above, the diffusion means 20 is configured to transmit the detection target gas such that the detection target gas flowing down through the gas flow path 10 can naturally diffuse toward the conversion portion 30, but it is desirable to configure the diffusion means 20 such that the conversion gas produced in the conversion portion 30 cannot easily permeate through the diffusion means 20 and migrate toward the gas flow path 10. That is, if the conversion gas cannot easily migrate toward the gas flow path 10, the conversion gas can be efficiently detected by the sensor element portion 30B. For this reason, with the diffusion means 20 described above, by variously setting, in addition to the hole diameter of the hole portions 21a and the number of hole portions 21a, the positions of the hole portions 21a, and also variously changing the air permeability of the porous film 22, it is possible to specify the air resistance of the diffusion means 20 such that the detection target gas used can naturally diffuse toward the conversion portion 30, and the conversion gas cannot easily migrate from the conversion portion 30 toward the gas flow path 10.

For example, in the case where the diffusion means 20 is configured by stacking the resin film 21 and the gas permeable porous film 22 together, the conversion rate can be set to about 35 to 90% by forming one hole portion 21a at the center of the resin film 21, and setting the hole diameter to 1 to 4 mm.

In the case where the diffusion means 20 is formed using a single material, it is possible to use, for example, a resin film that has a hole portion having a predetermined hole diameter, a gas permeable porous film, or the like, but the diffusion means 20 is not limited thereto.

The resin film may be a thin film obtained by molding a polymer component such as a plastic synthetic resin as listed above, but the resin film is not limited thereto. In this case as well, one or more hole portions having a predetermined hole diameter are formed in the resin film. The amount of detection target gas that permeates through the diffusion means 20 and naturally diffuses into the conversion portion 30 can be adjusted by setting the hole diameter of the hole portions 21a and the number of hole portions. For this reason, the hole diameter of the hole portions and the number of hole portions may be set so as to attain a desired amount of detection target gas. For example, if the resin film has an outer diameter of 14 mm, the hole diameter may be set to 1 to 4 mm.

As the porous film, it is possible to use, for example, a PTFE film as described above or the like. In the case where the diffusion means 20 is formed using a single material, it is possible to use the same single material (porous PTFE film), or a combination of a plurality of porous PTFE films that have different air permeabilities.

With this configuration, it is possible to adjust the amount of detection target gas that permeates through the diffusion means 20 and naturally diffuses into the conversion portion 30, with the use of a simple configuration. The amount of detection target gas may be adjusted by setting the hole diameter of the hole portions and the number of hole portions so as to attain a desired amount of detection target gas.

The conversion portion 30 is configured to detect the conversion gas produced by oxidizing the detection target gas, and thus includes a heated catalyst portion 30A and a sensor element portion 30B. The conversion portion 30 according to the present embodiment is formed as a portion of the internal space of a casing 1. That is, the interior of the casing 1 is divided by the diffusion means 20, and one of the regions formed by dividing the interior of the casing 1 is used as the conversion portion 30, and the other region is used as a portion of the gas flow path 10. The casing 1 may have any shape such as a cylindrical shape or a cubic shape. In the present embodiment, a case will be described where the direction in which the detection target gas flows down through the gas flow path 10 is different from (substantially perpendicular to) the direction in which a portion of the detection target gas permeates through the diffusion means 20 and naturally diffuses into the conversion portion 30. In this case, it is possible to easily allow at least a portion of the detection target gas flowing down through the gas flow path 10 to pass through the pores of the diffusion means 20 and naturally diffuse into the conversion portion 30 in a state in which it is unlikely to be influenced by the flow pressure of the detection target gas.

The heated catalyst portion 30A produces a conversion gas by causing the detection target gas that has permeated through the diffusion means 20 and naturally diffused into the conversion portion 30 to come into contact with the heated catalyst 31 and undergo oxidation. In the present embodiment, the following description will be given assuming that the catalyst 31 is a noble metal catalyst that contains Pd and Pt, but the catalyst is not limited thereto. It is also possible to use Ru, Rh, and Ir. The heated catalyst portion 30A may be configured to be heated, for example, up to 300 to 700° C., preferably up to 350 to 600° C., and more preferably up to about 400 to 600° C. In this case, the applied voltage is preferably set to about 0.68 to 1.85 V. When the detection target gas comes into contact with the heated catalyst 31, the detection target gas is oxidized, and also with the oxidation effect of the catalyst, the conversion gas is produced. If only one heated catalyst portion is provided, it is possible to suppress power consumption, but the number of heated catalyst portions is not limited to one, and a plurality of heated catalyst portions may be provided.

In the case where a plurality of heated catalyst portions are provided, for example, the following configurations are possible: a configuration in which two heated catalyst portions are provided in parallel with a predetermined distance therebetween, and the sensor element portion 30B is provided on the downstream side of the two heated catalyst portions; and a configuration in which two heated catalyst portions are provided to oppose each other in the casing 1. Also, in the case where a plurality of heated catalyst portions are provided, the heating temperatures of the heated catalyst portions may be set to the same temperature, or may be set to appropriate different temperatures according to their installation positions. The temperatures are preferably set such that the diffusion means 20 can appropriately exhibit its capabilities.

In the present embodiment, a case will be described where a contact combustion-type sensor element is used as the heated catalyst portion 30A. In this case, it is possible to configure a simple and miniaturized heated catalyst portion.

A contact combustion-type sensor includes a detection element that responds to a predetermined gas. The detection element is a contact combustion-type element formed by coating the surface of a coil of a metal wire that contains platinum or the like that has a high temperature coefficient of electric resistance with a carrier such as alumina that carries a noble metal catalyst that is active to the detection target gas. As the noble metal catalyst, it is possible to use fine particles of at least one or more of Pt, Pd, Ru, Rh, and Ir that are elements of the platinum group described above.

The detection element may have a spherical diameter of 0.76 to 1.08 mm, and preferably 0.84 to 1.00 m. When the spherical diameter is within the above range, it is possible to oxidize the detection target gas and produce the conversion gas with excellent efficiency.

As described above, in the present embodiment, the detection target gas is nitrogen trifluoride, and the conversion gas is nitrogen dioxide. It is considered that the conversion proceeds as shown by the following chemical reaction formulas Chem. 1 to Chem. 3.

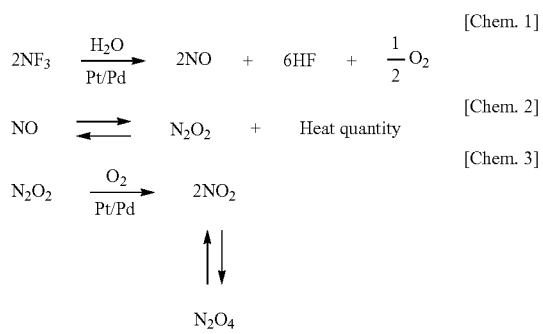

[Chem. 1]
[Chem. 2]
[Chem. 3]

As the sensor element portion 30B, it is possible to use an electrochemical sensor, an optical sensor, a semiconductor type gas sensor, a contact combustion-type sensor, or the like. In the present embodiment, a case will be described where the sensor element portion 30B is an electrochemical nitrogen oxide sensor element that contains noble metal carrying carbon and is configured to be capable of detecting nitrogen dioxide that is the produced conversion gas.

The electrochemical nitrogen oxide sensor element can be formed by housing, in a sensor case, a detection electrode that is a gas diffusion electrode, an auxiliary phase attached unitarily to the detection electrode, an electrolyte that is a normal temperature molten salt, and a counter electrode that has the same configuration as that of the detection electrode. The detection electrode is formed using a mixture of a carbon powder (gold carrying carbon) that carries a gold catalyst with polytetrafluoroethylene that serves as a binder. The auxiliary phase is formed by filling the pores of a porous nickel sheet with lithium nitrate that is an auxiliary phase material. This electrochemical nitrogen oxide sensor element is highly sensitive to nitrogen dioxide.

Gold carrying carbon can be pulverized into fine particles as fine as about 10 nm, and thus the electrochemical nitrogen oxide sensor element can be miniaturized. In addition, by pulverizing gold carrying carbon into fine particles, the surface area increases, and thus the sensitivity to nitrogen dioxide can be also improved.

Nitrogen trifluoride used in the present invention as the detection target gas is a gas to which the sensitivity of a gas sensor is low and that cannot be detected directly through an electrochemical reaction. For this reason, nitrogen trifluoride is subjected to oxidation and converted to nitrogen dioxide ($NO_2$) in advance. By doing so, it is possible to detect nitrogen trifluoride.

The catalytic conversion-type sensor X according to the present invention may further include a pump that draws the detection target gas to make it flow down, a flow rate sensor, a computation means that determines whether leakage of the detection target gas has occurred based on the result of detection of the sensor element portion 30B, and an alarm means that performs control so as to sound an alarm if a detection target gas concentration that is greater than or equal to an alarm level is continuously detected (all of which are provided outside the sensor and thus are not shown), as well as members such as an alarm device and a gas detector.

With the catalytic conversion-type sensor X according to the present invention, the diffusion means 20 allows the detection target gas flowing down through the gas flow path 10 to naturally diffuse toward the conversion portion 30. Accordingly, the amount of detection target gas that migrates to the conversion portion 30 can be made less dependent on the flow rate of the detection target gas that flows down through the gas flow path 10. For this reason, even if the flow rate sensor degrades and the flow rate of the detection target gas flowing down through the gas flow path 10 varies over time, the amount of detection target gas that migrates to the conversion portion 30 is unlikely to be directly affected, and thus the amount of detection target gas that migrates to the conversion portion 30 is unlikely to vary. Accordingly, with the catalytic conversion-type sensor X according to the present invention, the conversion rate for converting the detection target gas to the conversion gas is unlikely to be affected by the flow rate of the detection target gas, and thus the conversion rate is unlikely to decrease over time.

With the diffusion means 20 described above, the detection target gas that naturally diffuses into and stays in the conversion portion 30 can be efficiently brought into contact with the heated catalyst portion 30A, and thus the conversion rate can be improved to about 35 to 90%, and preferably to about 45 to 90%. At this time, the detection target gas is oxidized by the heated catalyst portion 30A, and also with the oxidation effect of the catalyst, the conversion gas is produced. Accordingly, the heating temperature of the heated catalyst portion 30A can be suppressed to 300 to 700° C., preferably to 350 to 600° C., more preferably to 400 to 600° C., and even more preferably to about 450° C. When the heating temperature is within the above temperature range, it is possible to achieve both a response rate and detectable sensitivity.

With the diffusion means 20 described above, it is possible to make it difficult for the conversion gas to migrate from the conversion portion 30 to the outside (the gas flow path 10), and thus the conversion gas that stays in the conversion portion 30 can be efficiently and stably detected by the sensor element portion 30B.

Also, with the catalytic conversion-type sensor X according to the present invention, the conversion portion 30 includes the heated catalyst portion 30A and the sensor element portion 30B, and thus it is unnecessary to additionally provide a thermal decomposition unit, and therefore miniaturization can be achieved.

Other Embodiments

The foregoing described a catalytic conversion-type sensor X configured to detect a conversion gas produced through an oxidation reaction, but the configuration is not limited thereto. The catalytic conversion-type sensor X according to the present invention may also be configured to detect a conversion gas produced through a thermal decomposition reaction.

In the present embodiment, a case will be described in which the detection target gas is hexafluoro-1,3-butadiene ($C_4F_6$), and the sensor element portion 30B is a hydrogen fluoride sensor that is an electrochemical sensor element capable of detecting hydrogen fluoride (HF), but the configuration is not limited thereto. For example, the detection target gas may be $C_5F_8$ or $C_4F_8$, and the sensor element portion 30B may be a fluorine sensor capable of detecting fluorine ($F_2$).

A diffusion means 20 according to the present embodiment may be configured to cause, as with the detection target gas that permeates from the gas flow path 10 through the film and reaches an equilibrium at a certain concentration, the conversion gas to reach an equilibrium at a concentration corresponding to the concentration of the detection target gas without causing the conversion gas to stay in the conversion portion 30, and discharge the conversion gas to the gas flow path 10.

The diffusion means 20 may be formed by combining different materials, or may be formed using a single material. However, it is preferable that the diffusion means 20 includes at least a porous film. In the case where the diffusion means 20 is formed using only a porous film, as with the detection target gas that permeates from the gas flow path 10 through the film and reaches an equilibrium at a certain concentration, the conversion gas is likely to reach an equilibrium at a concentration corresponding to the concentration of the detection target gas without staying in the conversion portion 30, and can be easily discharged to the gas flow path 10.

For example, in the case where the diffusion means 20 is formed by combining different materials, as shown in FIG. 2, the diffusion means 20 can be formed by adjacently providing and stacking together a resin film 21 that has a hole portion 21a having a predetermined hole diameter and a gas permeable porous film 22. The resin film 21 and the gas permeable porous film 22 may have the same configurations as those described in the embodiment given above.

At this time, the porous film 22 can be configured to have a desired porosity such that as with the detection target gas that permeates from the gas flow path 10 through the film and reaches an equilibrium at a certain concentration, the conversion gas is likely to reach an equilibrium at a concentration corresponding to the concentration of the detection target gas without staying in the conversion portion, and can be easily discharged to the flow path.

The conversion portion 30 is configured to detect the conversion gas produced by thermally decomposing the detection target gas, and thus includes a heated catalyst portion 30A and a sensor element portion 30B. In the present embodiment as well, as shown in FIG. 1, the conversion portion 30 is formed as a portion of the internal space of a casing 1. That is, the interior of the casing 1 is divided by the diffusion means 20 (FIGS. 1 and 2), and one of the regions formed by dividing the interior of the casing 1 is used as the conversion portion 30, and the other region is used as a portion of the gas flow path 10. The casing 1 may have any shape such as a cylindrical shape or a cubic shape. In the present embodiment as well, a case will be described where the direction in which the detection target gas flows down through the gas flow path 10 is different from (substantially perpendicular to) the direction in which a portion of the detection target gas permeates through the diffusion means 20 and naturally diffuses into the conversion portion 30.

The heated catalyst portion 30A produces a conversion gas by causing the detection target gas that has permeated through the diffusion means 20 and naturally diffused into the conversion portion 30 to come into contact with a heated catalyst 31 and undergo thermal decomposition. In the present embodiment as well, the following description will be given assuming that the catalyst 31 is a noble metal catalyst that contains Pd and Pt, but the catalyst is not limited thereto. It is also possible to use Ru, Rh, and Ir. The heated catalyst portion 30A may be configured to be heated, for example, up to about 400 to 600° C., and preferably up to about 450° C. When the detection target gas comes into contact with the heated catalyst 31, the detection target gas is thermally decomposed, and a conversion gas is thereby produced. If only one heated catalyst portion is provided, it is possible to suppress power consumption, but the number of heated catalyst portions is not limited to one, and a plurality of heated catalyst portions may be provided. In the present embodiment as well, in the case where a plurality of heated catalyst portions are provided, for example, the following configurations are possible: a configuration in which two heated catalyst portions are provided in parallel with a predetermined distance therebetween, and the sensor element portion 30B is provided on the downstream side of the two heated catalyst portions; and a configuration in which two heated catalyst portions are provided opposing each other in the casing 1. Also, in the case where a plurality of heated catalyst portions are provided, the heating temperatures of the heated catalyst portions may be set to the same temperature, or may be set to appropriate different temperatures according to their installation positions. The temperatures are preferably set such that the diffusion means 20 can appropriately exhibit its capabilities. Because the catalyst 31 is provided, even when the temperatures are relatively low, thermal decomposition can take place.

In the present embodiment as well, a case will be described where a contact combustion-type sensor element is used as the heated catalyst portion 30A.

The contact combustion-type sensor includes a detection element that responds to a predetermined gas. The detection element may have the same configuration as that described in the embodiment given above.

As described above, in the present embodiment, the detection target gas is $C_4F_6$, and the conversion gas is hydrogen fluoride. It is considered that the conversion proceeds as shown by the following chemical reaction formula Chem. 4.

$$C_4F_6 + 3H_2O + 5/2O_2 \rightarrow 6HF + 4CO_2 \quad \text{[Chem. 4]}$$

As the sensor element portion 30B, it is possible to use an electrochemical sensor, an optical sensor, a semiconductor type gas sensor, a contact combustion-type sensor, or the like. In the present embodiment, a case will be described where the sensor element portion 30B is an electrochemical sensor element that contains noble metal carrying carbon, and is configured to be capable of detecting hydrogen fluoride that is the produced conversion gas.

As in the embodiment described above, the electrochemical sensor element can be formed by housing, in a sensor case, a detection electrode that is a gas diffusion electrode, an auxiliary phase attached unitarily to the detection electrode, an electrolyte that is a normal temperature molten salt, and a counter electrode that has the same configuration as that of the detection electrode. The detection electrode is formed using a mixture of a carbon powder (gold carrying carbon) that carries a gold catalyst with polytetrafluoroethylene that serves as a binder. The auxiliary phase is formed by filling the pores of a porous nickel sheet with lithium nitrate that is an auxiliary phase material. This electrochemical sensor element is also highly sensitive to hydrogen fluoride.

Gold carrying carbon can be pulverized into fine particles as fine as about 10 nm, and thus the electrochemical sensor element can be miniaturized. In addition, by pulverizing gold carrying carbon into fine particles, the surface area thereof increases, and thus the sensitivity to hydrogen fluoride can be also improved.

$C_4F_6$ that is used in the present invention as the detection target gas is a gas to which the sensitivity of a gas sensor is low and that cannot be detected directly through an electrochemical reaction. For this reason, $C_4F_6$ is subjected to thermal decomposition and converted to hydrogen fluoride in advance. By doing so, it is possible to detect $C_4F_6$.

In the present embodiment as well, as in the embodiment described above, the diffusion means 20 allows the detection target gas flowing down through the gas flow path 10 to naturally diffuse toward the conversion portion 30. Accordingly, the amount of the detection target gas that migrates to the conversion portion 30 can be made less dependent on the flow rate of the detection target gas that flows down through the gas flow path 10. For this reason, the conversion rate for converting the detection target gas to the conversion gas is unlikely to be affected by the flow rate of the detection target gas, and thus the conversion rate is unlikely to decrease over time.

Furthermore, with the catalytic conversion-type sensor X according to the present embodiment, the conversion portion 30 includes the heated catalyst portion 30A and the sensor element portion 30B, and thus it is unnecessary to use a large thermal decomposition furnace, and therefore miniaturization can be achieved.

EXAMPLES

Example 1

Examples according to the present invention will be described.

Variations in the conversion rate were checked by using the catalytic conversion-type sensor X according to the present invention.

The detection target gas was nitrogen trifluoride, the conversion gas was nitrogen dioxide, and the sensor element portion 30B was an electrochemical nitrogen oxide sensor element. Also, the diffusion means 20 was formed by stacking together a circular resin film (plastic synthetic resin) 21 and a gas permeable porous film (PTFE film) 22, with the resin film 21 having one hole portion 21a formed at the center of the resin film 21. Variations in the conversion rate were checked by variously changing the hole diameter of the hole portions 21a from φ1 to 14 mm. φ14 mm indicates a size corresponding to the diameter of a conversion portion 30 having a cylindrical shape.

Figure 3:
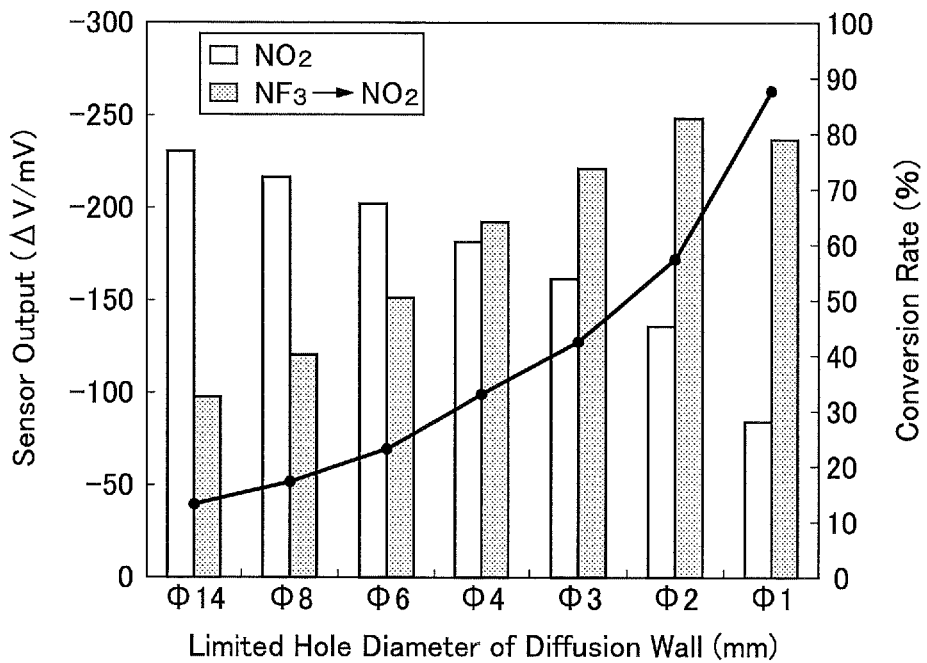
FIG. 3 is a graph showing the results of variations in the conversion rate obtained by variously changing the hole diameter of a hole portion formed in a resin film included in the diffusion means.

Gases that were caused to flow down were nitrogen trifluoride and nitrogen dioxide, and the gases were caused to flow down separately. The reason that nitrogen dioxide was caused to flow down was to check how nitrogen dioxide would behave depending on the hole diameter of the hole portions 21a. The results are shown in FIG. 3. In the case where nitrogen trifluoride was caused to flow down, the sensor output of nitrogen dioxide, which was the conversion gas produced in the conversion portion 30, was measured. In the case where nitrogen dioxide was caused to flow down, the sensor output of nitrogen dioxide that naturally diffused into the conversion portion 30 was measured.

As a result, in the case where nitrogen dioxide was caused to flow down, the sensor output was high when the hole diameter was large (φ8 to 14), from which it was found that nitrogen dioxide is likely to naturally diffuse to the conversion portion 30. However, in this case, nitrogen dioxide is also likely to migrate from the conversion portion 30 to the outside (the gas flow path 10).

In the case where nitrogen trifluoride was caused to flow down, the sensor output was low when the hole diameter was large (φ8 to 14), and thus the conversion rate was about 10 to 20%. This is presumably because, due to the hole diameter being large, nitrogen dioxide that was the conversion gas produced from nitrogen trifluoride could easily migrate from the conversion portion 30 to the outside (the gas flow path 10). On the other hand, when the hole diameter was small (φ1 to 4), the sensor output was high, and thus the conversion rate was about 35 to 90%. This is presumably because, due to the hole diameter being small, nitrogen dioxide that was the conversion gas produced from nitrogen trifluoride could not easily migrate from the conversion portion 30 to the outside (the gas flow path 10), and thus nitrogen dioxide was efficiently detected.

From the above, it can be seen that, with the use of the resin film 21 having one hole portion 21a formed therein, a good conversion rate of about 35 to 90% can be obtained when the hole diameter is set to 1 to 4 mm, and preferably a good conversion rate of about 45 to 90% can be obtained when the hole diameter is set to 1 to 3 mm.

Example 2

The catalytic conversion-type sensor X according to the present invention was compared with a conventional sensor in terms of sensitivity for detecting nitrogen trifluoride. As the conventional sensor, a sensor was used that was configured to, in order to convert nitrogen trifluoride to nitrogen dioxide through thermal decomposition so as to detect nitrogen dioxide, thermally decompose the detection target gas at a thermal decomposition unit additionally provided in advance and introduce the detection target gas to a sensor portion. A thermal decomposition unit having a known configuration was used as the thermal decomposition unit.

Figure 4:
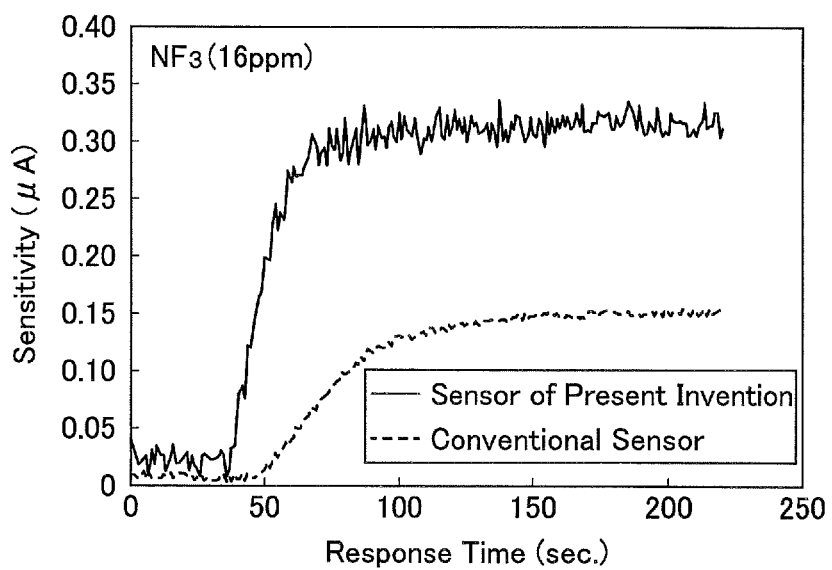
FIG. 4 is a graph showing the results of detection of nitrogen trifluoride obtained by using the catalytic conversion-type sensor according to the present invention and by using a conventional sensor.

The diffusion means 20 had an air resistance of 50 mm·Pa$^{-1}$·s$^{-1}$, the resin film 21 was a resin film (with a resin film diameter of 16 mm, and a PP film thickness of 0.2 mm) that had one hole portion 21a (with a hole diameter of 6 mm) formed at its center, and the porous film was a porous PTFE film (available from Tomoegawa Co., Ltd.). Also, the conversion portion 30 had a volume of 0.001 m$^3$, and the heating temperature of the heated catalyst portion 30A was 450° C. Furthermore, the nitrogen trifluoride concentration was 16 ppm. In the catalytic conversion-type sensor X according to the present invention and the conventional sensor, the flow rate at which the gas was caused to flow down through the gas flow path was 0.5 L/min. The results obtained by detecting nitrogen trifluoride using each sensor are shown in FIG. 4.

As a result, the sensitivity of the catalytic conversion-type sensor X according to the present invention to nitrogen trifluoride reached a value as high as around 0.30 μA after 50 seconds, but the sensitivity of the conventional sensor to nitrogen trifluoride had a value as low as around 0.15 μA even after 100 seconds. Accordingly, it was found that the catalytic conversion-type sensor X according to the present invention is a highly sensitive sensor that can achieve a high conversion rate.

Example 3

Figure 5:
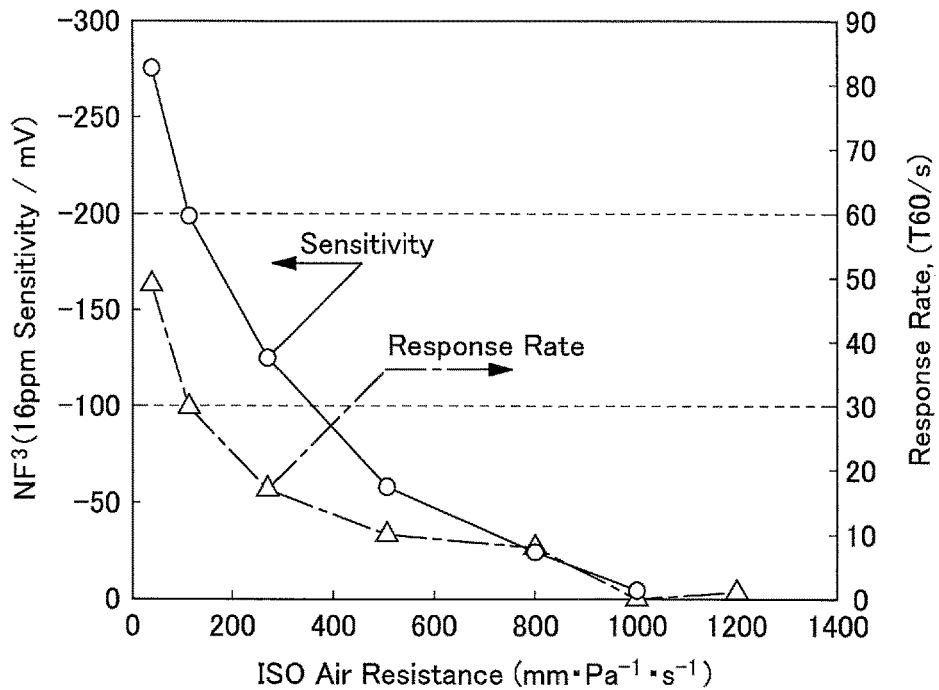
FIG. 5 is a graph showing the results of the air resistance of the diffusion means.

The air resistance of the diffusion means 20 of the catalytic conversion-type sensor X used in Example 2 was checked. The air resistance was variously changed by variously changing the configuration of the diffusion means 20, and the range of air resistance for obtaining a sufficient gas sensitivity was determined by taking into consideration a response rate of less than or equal to 60 seconds, and preferably less than or equal to 30 seconds as a reference value. The diffusion means 20 was formed using only a PP film (without a porous PTFE sheet), and the hole diameter of the hole portions 21a was set to 1 mm, 2 mm, 3 mm, 4 mm, 6 mm, 8 mm, and 14 mm (maximum). The air resistance was set to 50, 100, 150, 300, 800, 1000, and 1200 in ascending order of the hole diameter. The results are shown in FIG. 5.

As a result, it was found that when the air resistance of the diffusion means is 800 mm·Pa$^{-1}$·s$^{-1}$ or less, a preferred response rate (less than or equal to 60 seconds) is satisfied. Furthermore, it was found that when the air resistance of the diffusion means is 50 to 800 mm·Pa$^{-1}$·s$^{-1}$, a sufficient gas sensitivity (25 mV or more) is satisfied.

Example 4

With respect to the catalytic conversion-type sensor X according to the present invention, the relationship between gas sensitivity and response time was checked by using each of the following configurations: a configuration in which a resin film made of a single material was used as the diffusion means 20 (Example 4-1); and a configuration in which a resin film 21 and a porous film 22 were adjacently provided and stacked together (Example 4-2).

Figure 6:
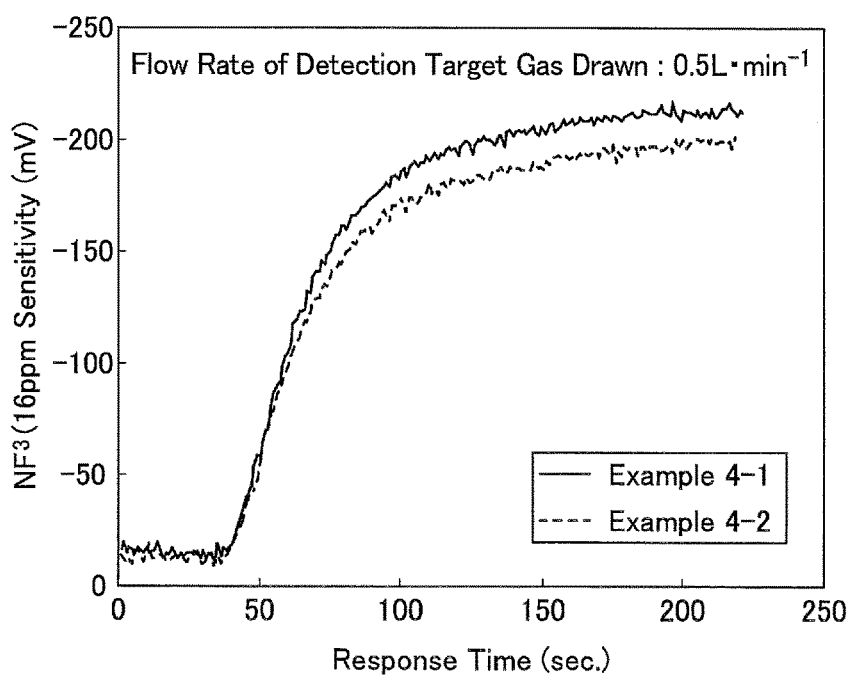
FIG. 6 is a graph showing the relationship between gas sensitivity and response time obtained by using diffusion means of different configurations.

In the sensor of Example 4-1, a diffusion means 20 formed by making a hole portion having a hole diameter of 2 mm in a resin film having a film diameter of 14 mm was used. In the sensor of Example 4-2, a diffusion means 20 formed using a resin film 21 having a film diameter of 14 mm and a hole portion having a hole diameter of 4 mm and a porous PTFE film having a film diameter of 14 mm was used. The nitrogen trifluoride concentration was 16 ppm. The results are shown in FIG. 6.

As a result, it was found that in both examples, a high gas sensitivity of about 160 to 210 mV can be obtained after about 100 to 200 seconds.

Example 5

The dependency of the reading value obtained at the time of gas detection on the flow rate of the detection target gas was checked by using the catalytic conversion-type sensor X according to the present invention and a conventional sensor. The conventional sensor 1 used in Example 2 was used as the conventional sensor.

Figure 7:
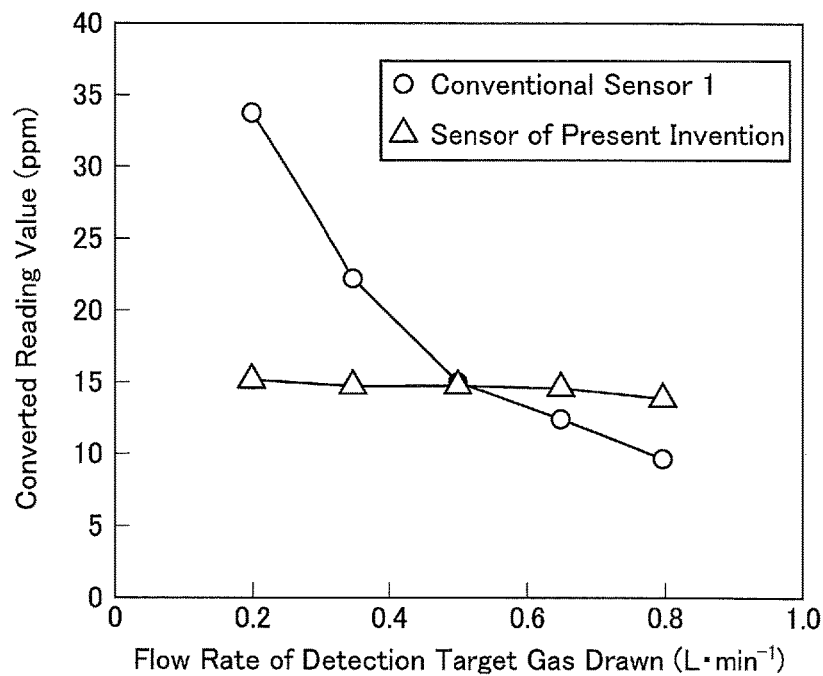
FIG. 7 is a graph showing the results of dependency of the reading value obtained at the time of gas detection on the flow rate of detection target gas.

The detection target gas was nitrogen trifluoride at a concentration of 15 ppm, and the flow rate was variously changed within a range from 0.2 to 0.8 L/min. The results are shown in FIG. 7.

As a result, in the conventional sensor 1, the conversion rate decreased as the flow rate increased, and thus the reading value decreased, but in the catalytic conversion-type sensor X according to the present invention, the reading value remained almost unchanged even when the flow rate was increased. For this reason, the catalytic conversion-type sensor X according to the present invention was found to be less dependent on the flow rate of the detection target gas.

Example 6

The relationship between applied voltage and element temperature was checked in the case where a contact combustion-type sensor was used as the heated catalyst portion 30A by variously changing the spherical diameter of a detection element included in the contact combustion-type sensor.

Figure 8:
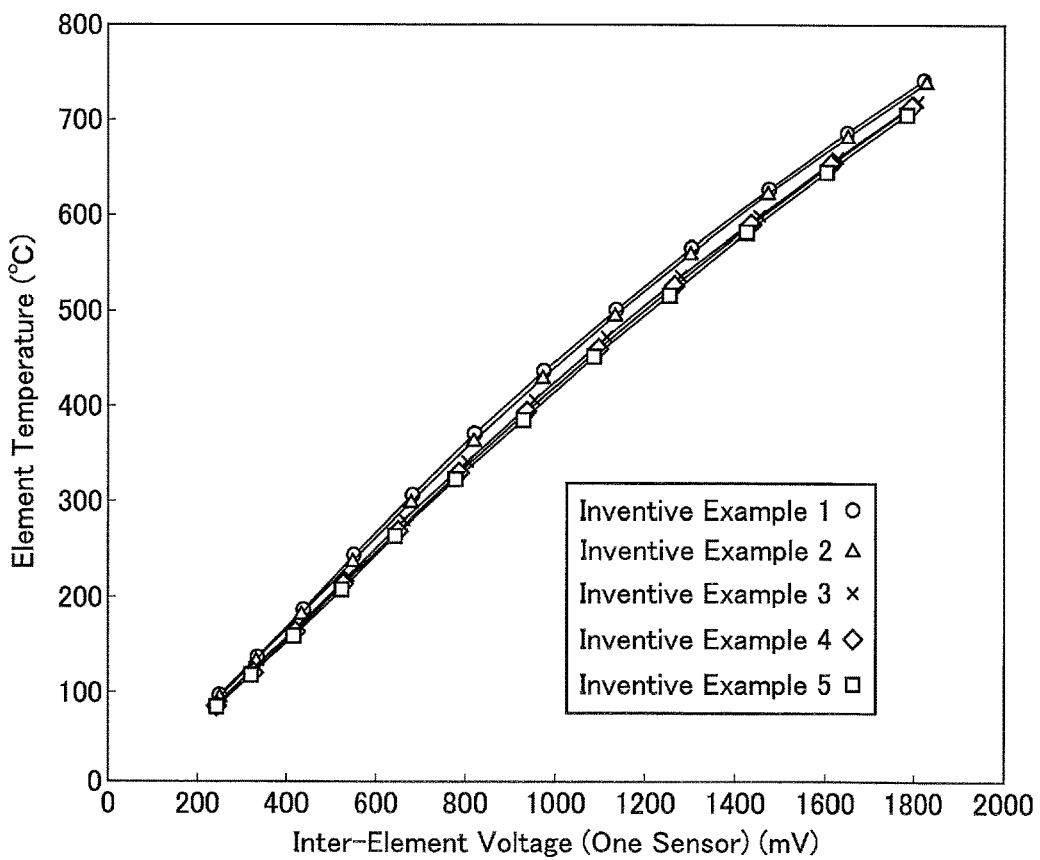
FIG. 8 is a graph illustrating the relationship between applied voltage (about 220 to 1820 mV) and element temperature obtained by variously changing the spherical diameter of a detection element included in a contact combustion-type sensor.
Figure 9:
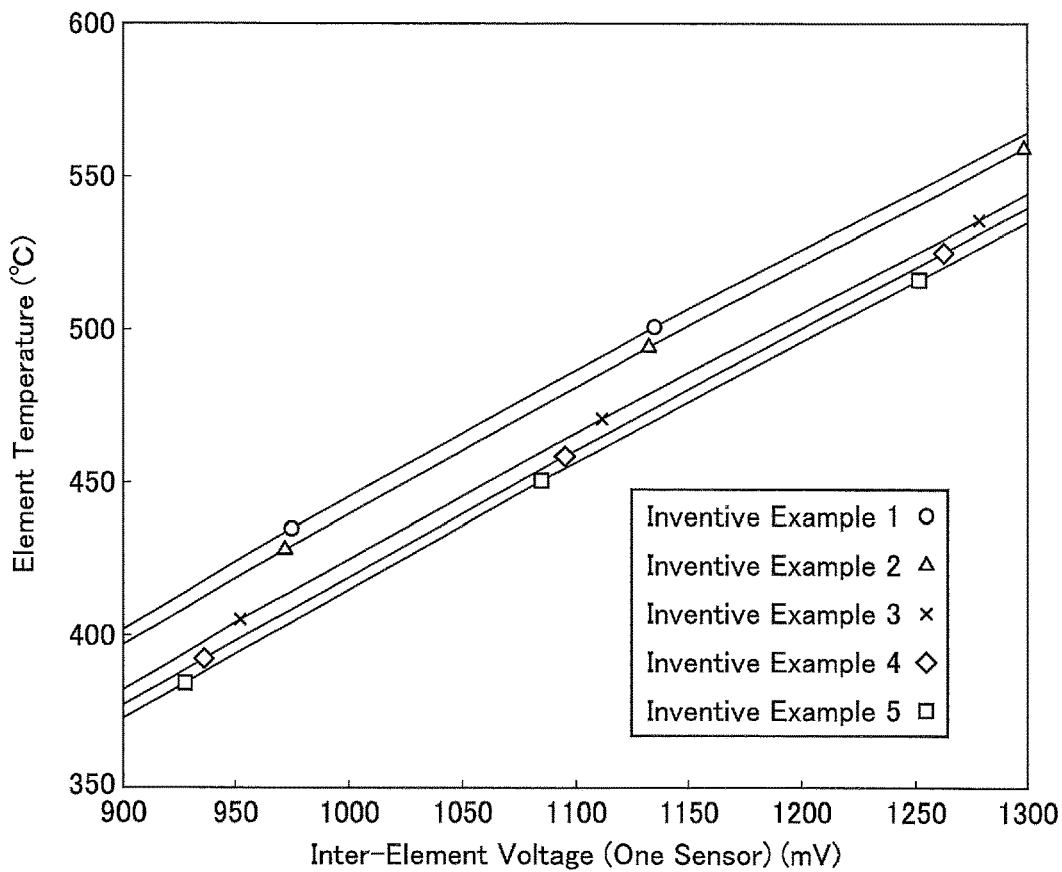
FIG. 9 is a graph illustrating the relationship between applied voltage (900 to 1300 mV) and element temperature obtained by variously changing the spherical diameter of the detection element included in the contact combustion-type sensor.

As the detection element, a detection element was used that was formed by coating a platinum coil with alumina carrying a noble metal catalyst that contained Pd and Pt, and the spherical diameter of the detection element was set to 0.76 mm (Inventive Example 1), 0.84 mm (Inventive Example 2), 0.92 mm (Inventive Example 3), 1.00 mm (Inventive Example 4), and 1.08 mm (Inventive Example 5). The element temperature was measured by changing the applied voltage within a range from about 220 to 1820 mV. The results are shown in FIGS. 8 and 9. FIG. 9 is an enlarged view of a part of the graph shown in FIG. 8 in which the applied voltage is set to 900 to 1300 mV.

As a result, it was found that the element temperature increases as the applied voltage increases, and the element temperature decreases as the spherical diameter of the detection element increases, with the same voltage.

Example 7

Figure 10:
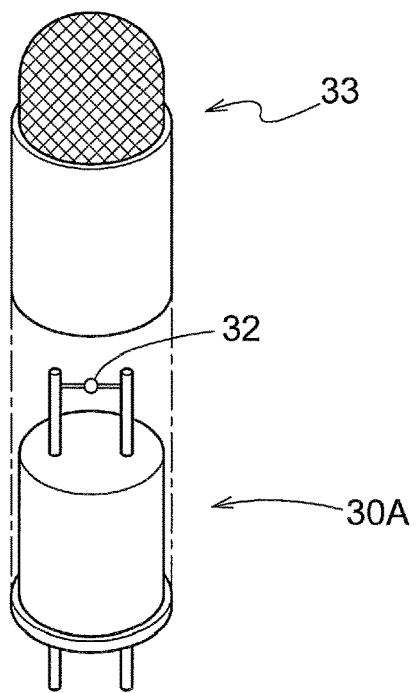
FIG. 10 is a schematic view of a cap configured to not limit diffusion (diffusion non-limiting cap).
Figure 11:
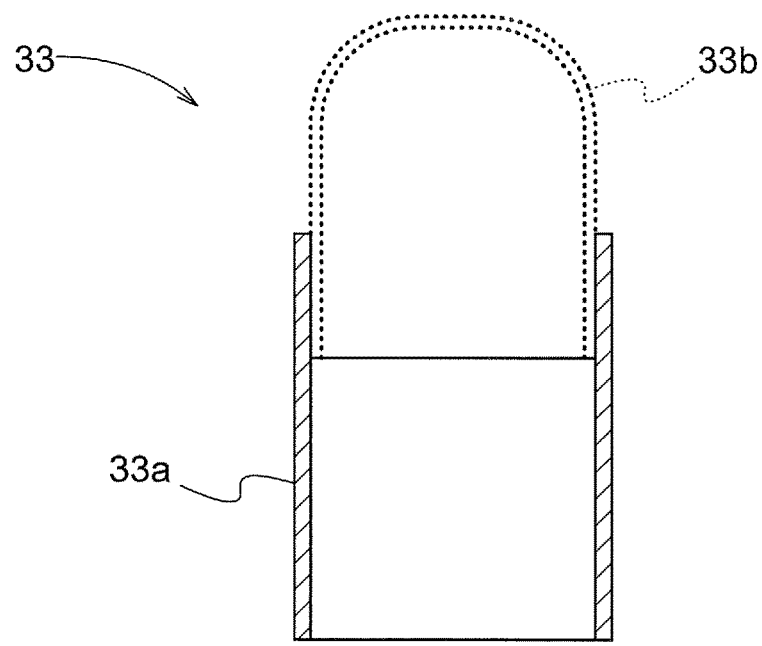
FIG. 11 is a schematic view of the cap configured to not limit diffusion (diffusion non-limiting cap).
Figure 12:
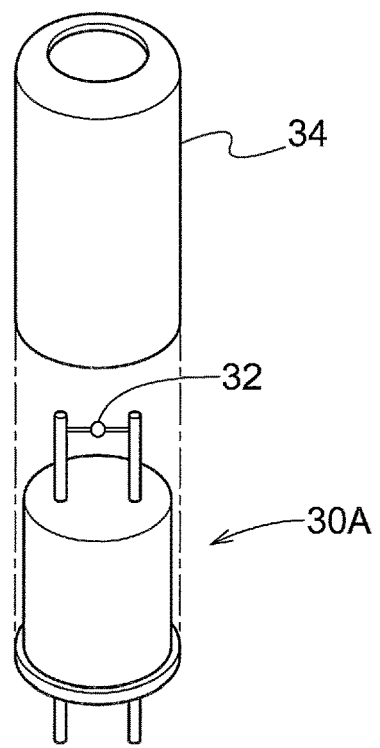
FIG. 12 is a schematic view of a cap configured to limit diffusion (diffusion limiting cap).
Figure 13:
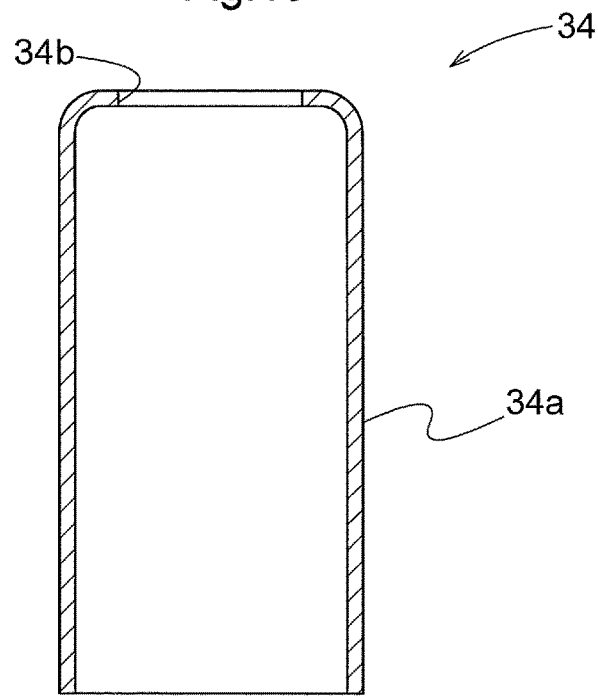
FIG. 13 is a schematic view of the cap configured to limit diffusion (diffusion limiting cap).

In the case where a contact combustion-type sensor was used as the heated catalyst portion 30A, by replacing a cap for covering a detection element 32 included in the contact combustion-type sensor with a cap 33 configured to not limit diffusion (FIGS. 10 and 11, hereinafter referred to as "diffusion non-limiting cap"), and a cap 34 configured to limit diffusion (FIGS. 12 and 13, hereinafter referred to as "diffusion limiting cap"), the influence of the spherical diameter of the detection element 32 was checked.

The diffusion non-limiting cap 33 was composed of a body portion 33a and a metal mesh portion 33b. The body portion 33a was a SUS 304 seamless tube that had a diameter of 5.8 to 5.9 mm and a flared shape, and the metal mesh portion 33b had a semicircular shape having a maximum diameter of 5.2 mm, and was formed using a double-structured 100 mesh SUS 316 metal mesh having a wire diameter of 0.1 mm. The metal mesh portion 33b was fitted into the body portion 33a by performing spot welding at four locations, and the length dimension when they were assembled was 11.5 mm. The diffusion non-limiting cap 33 was configured so as to not limit the diffusion of, for example, the gas within the diffusion non-limiting cap 33 via the metal mesh portion 33b of the diffusion non-limiting cap 33.

On the other hand, the diffusion limiting cap 34 was composed of a tubular SUS 305-2D body portion 34a having a diameter of 5.9 mm and a length dimension of 11.6 mm, and a hole portion 34b having a diameter of 3.6 mm formed in the body portion 34a. The diffusion limiting cap 34 was configured so as to limit the diffusion of, for example, the gas within the diffusion limiting cap 34 via the hole portion 34b of the diffusion limiting cap 34 to some degree by forming the hole portion 34b to have a hole diameter smaller than the diameter of the body portion 34a.

The diffusion limiting cap 34 was configured to limit the diffusion to about 50% of that of the diffusion non-limiting cap 33.

Methane gas was used as a test gas. The results of gas sensitivity obtained by changing the methane gas concentration from 0 to 100% LEL are shown in FIG. 14 (with the diffusion non-limiting cap 33) and FIG. 15 (with the diffusion limiting cap 34).

Figure 14:
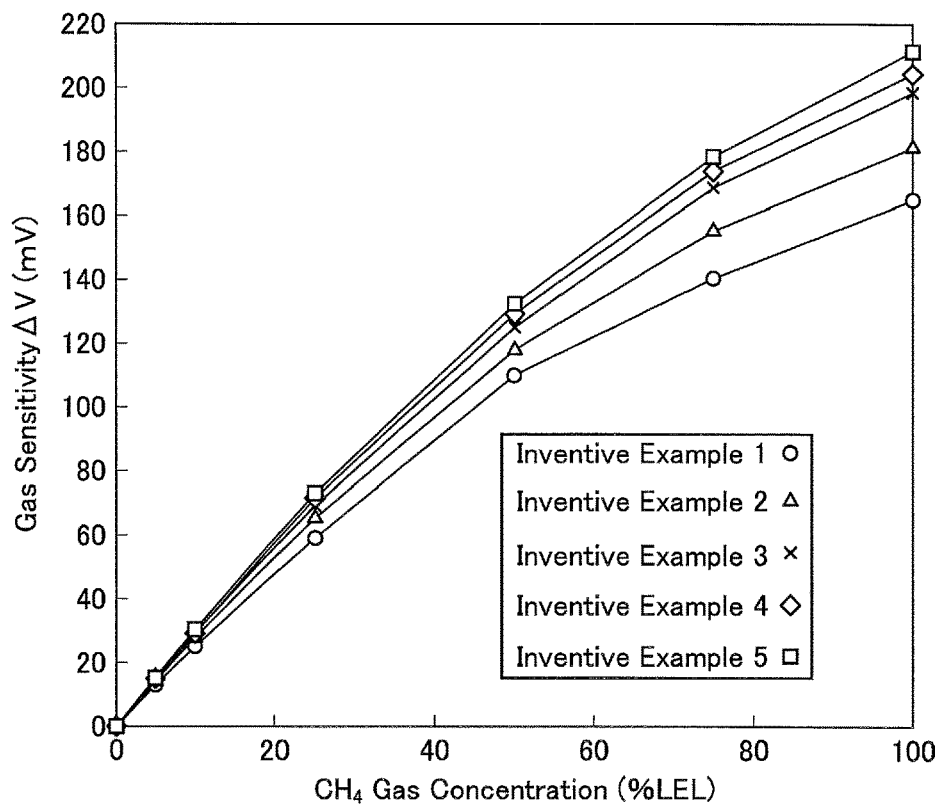
FIG. 14 is a graph showing the results of gas sensitivity obtained by changing the methane gas concentration from 0 to 100% LEL, with the use of the diffusion non-limiting cap.
Figure 15:
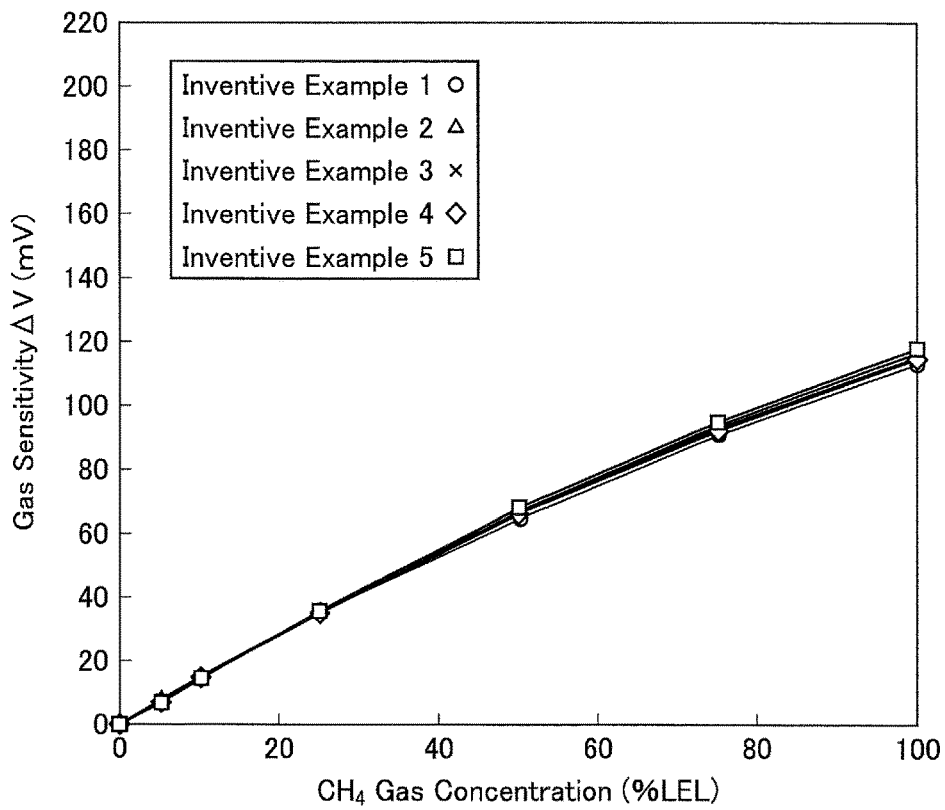
FIG. 15 is a graph showing the results of gas sensitivity obtained by changing the methane gas concentration from 0 to 100% LEL, with the use of the diffusion limiting cap.

As a result, it was found from FIG. 14 that in the case where the diffusion non-limiting cap 33 is used, the sensitivity increases as the spherical diameter of the detection element 32 increases, and it was also found from FIG. 15 that in the case where the diffusion limiting cap 34 is used, the sensitivity is hardly affected by the spherical diameter of the detection element 32. This is presumably because, due to the diffusion limiting function of the diffusion limiting cap 34, the difference in sensitivity created by changing the spherical diameter of the detection element 32 is small. Accordingly, it was found that in the case where the diffusion limiting cap 34 is used, even if, for example, the reactivity decreases due to degradation of the catalyst, the output value is unlikely to change, and the sensitivity decreases slightly.

As described above, in the case where the diffusion limiting cap 34 is used, the sensitivity is almost non-dependent on the spherical diameter. Accordingly, it is considered that, when a diffusion limiting cap is used, the state of gas diffusion in the heated catalyst portion 30A is diffusion controlled. That is, it is considered that the diffusion limiting cap 34 is a cap that does not lead to a change in the sensitivity even if the spherical diameter is intentionally changed. Furthermore, in this example, methane gas was used, but it is considered that even when the diffusion limiting cap 34 is used for a gas whose molecules are larger than those of methane gas and that is hard to diffuse, diffusion control is possible.

Example 8

In the case where a contact combustion-type sensor was used as the heated catalyst portion 30A, changes in the $NO_2$ sensitivity and the response rate of an electrochemical nitrogen oxide sensor element (the sensor element portion 30B) with respect to the spherical diameter of a detection element included in the contact combustion-type sensor were checked. The spherical diameter of the detection element was set to 0.76 mm to 1.08 mm, as in Example 6. The two types of caps used in Example 7 were used as the cap in the contact combustion-type sensor. The detection target gas was nitrogen trifluoride at a concentration of 16 ppm, and the applied voltage was 1.1 V. The results are shown in FIGS. 16 and 17.

Figure 16:
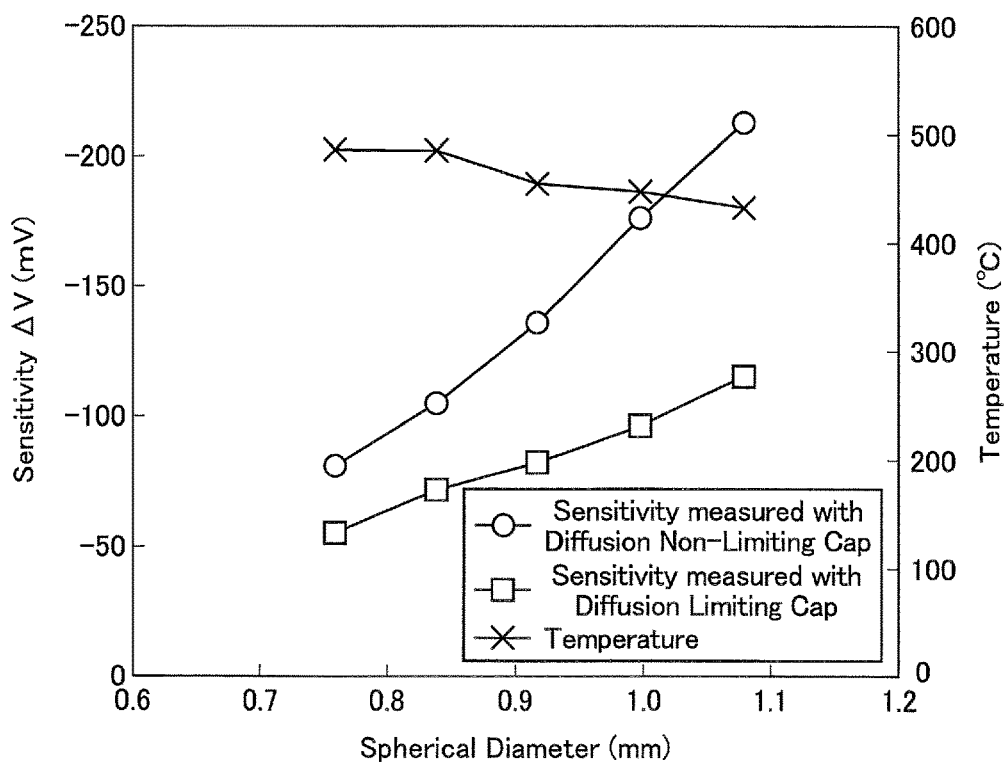
FIG. 16 is a graph showing the results of changes in the $NO_2$ sensitivity of the electrochemical nitrogen oxide sensor element relative to the spherical diameter of the detection element of the contact combustion-type sensor.
Figure 17:
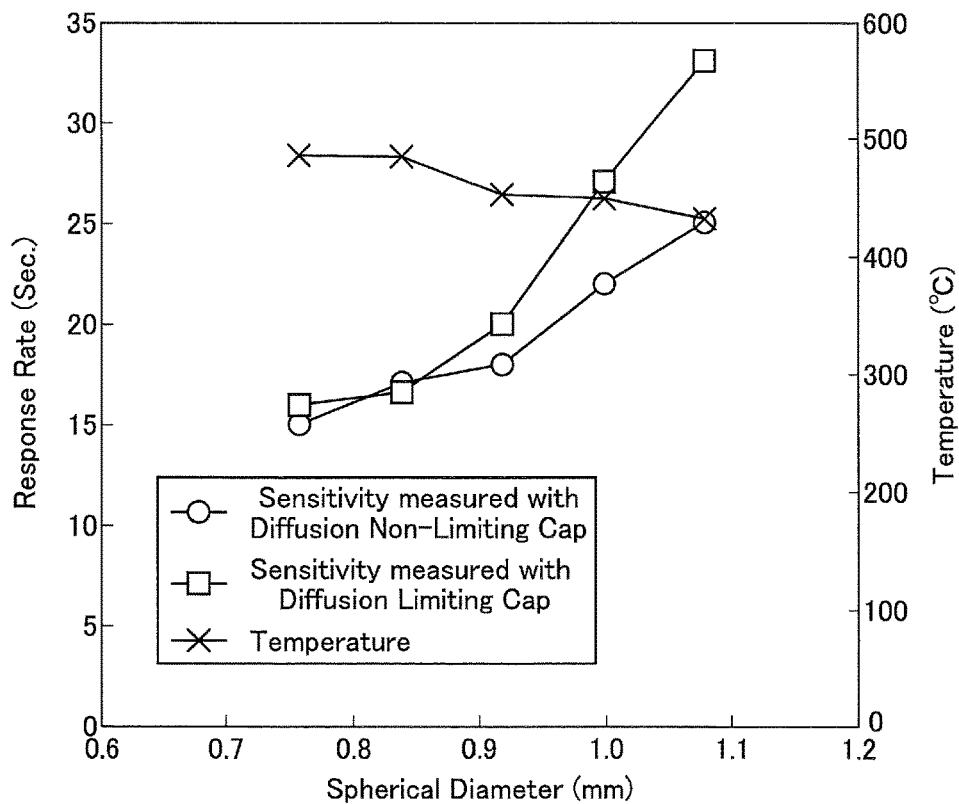
FIG. 17 is a graph showing the results of changes in the response rate of the electrochemical nitrogen oxide sensor element relative to the spherical diameter of the detection element of the contact combustion-type sensor.

As a result, it was found, irrespective of the caps used, from FIG. 16 that the sensitivity increases as the spherical diameter of the detection element increases, and it was also found from FIG. 17 that the response rate decreases as the spherical diameter increases. From these results, it was found that there is a practically optimal range for the spherical diameter of the detection element in relation to the sensitivity and the response rate. That is, for example, if a $NO_2$ sensitivity of, for example, 50 mV or more (FIG. 16) is required, by setting the spherical diameter of the detection element to 0.76 to 1.08 mm, a response rate of about 15 to 34 seconds (FIG. 17) can be obtained, as a result of which the detection target gas can be oxidized and the conversion gas can be produced with excellent efficiency, and a preferred response rate (less than or equal to 60 seconds) can be satisfied.

Also, in particular, it was found that when the spherical diameter of the detection element is set to 0.84 to 1.00 mm, a $NO_2$ sensitivity of 50 mV or more can be obtained (FIG. 16), and a response rate of less than or equal to 30 seconds can be satisfied (FIG. 17).

Example 9

In Example 8, changes in the $NO_2$ sensitivity and the response rate of the electrochemical nitrogen oxide sensor element (the sensor element portion 30B) with respect to the temperature of the detection element (the heated catalyst portion 30A) were checked. The spherical diameter of the detection element 32 was set to 1.00 mm. The results are shown in FIGS. 18 and 19.

Figure 18:
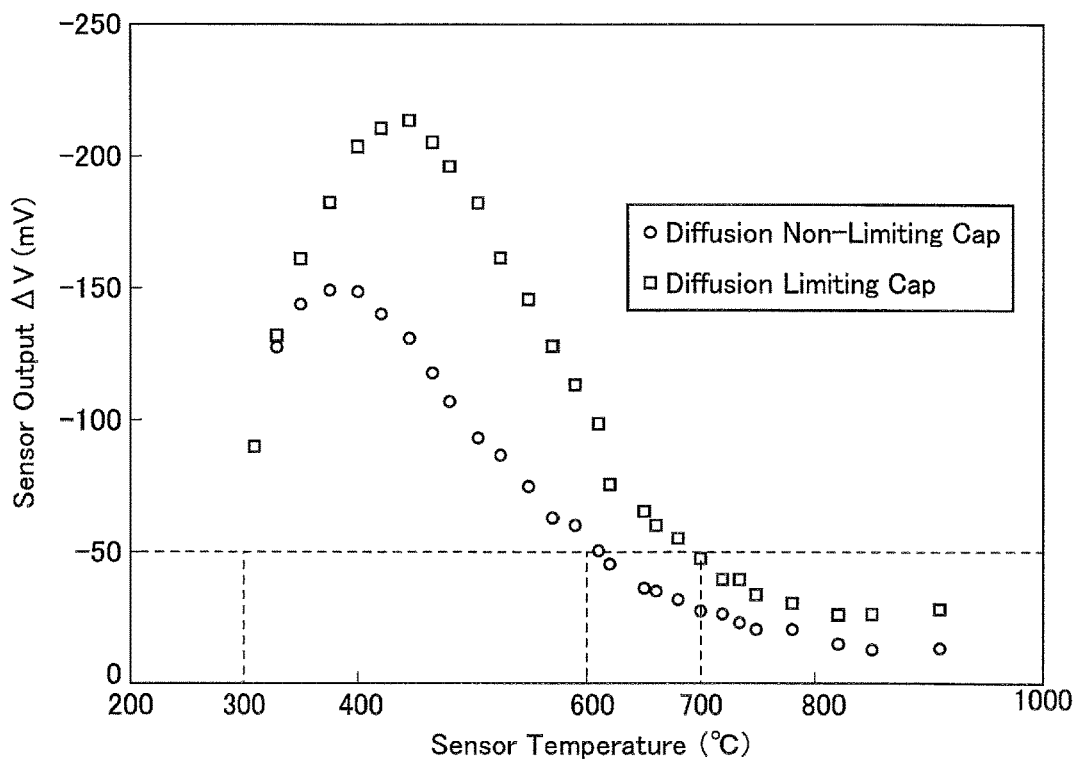
FIG. 18 is a graph showing the results of changes in the $NO_2$ sensitivity of the electrochemical nitrogen oxide sensor element relative to the temperature of the detection element of the contact combustion-type sensor.

From FIG. 18, it was found that, in the two types of caps, the top temperature of the detection element was different, but the sensor output peaks at around 400 to 420° C., and after that, the sensor output decreases as the temperature of the detection element increases. That is, it was found that, for example, if a $NO_2$ sensitivity of 50 mV or more is required, the temperature of the detection element is preferably set to 300 to 700° C. in the case where the diffusion non-limiting cap 33 is used, and the temperature of the detection element is preferably set to 300 to 600° C. in the case where the diffusion limiting cap 34 is used.

Figure 19:
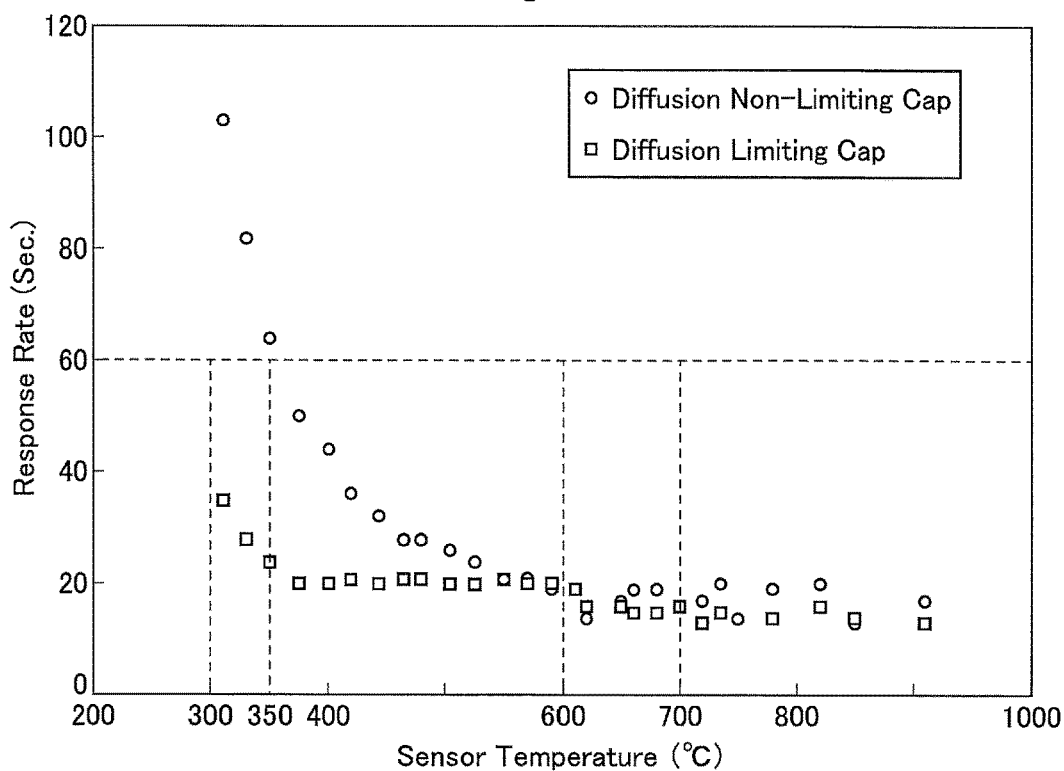
FIG. 19 is a graph showing the results of changes in the response rate of the electrochemical nitrogen oxide sensor element relative to the temperature of the detection element of the contact combustion-type sensor.

Also, from FIG. 19, it was found that, in the two types of caps, the response rate increases as the temperature of the detection element increases. That is, in the case where the diffusion non-limiting cap 33 is used, a preferred response rate (less than or equal to 60 seconds) is satisfied when the temperature of the detection element is around 300° C. or more, and the response rate remains almost unchanged after a temperature around 700° C., from which it was found that the temperature of the detection element is preferably set to 300 to 700° C. Also, in the case where the diffusion limiting cap 34 is used, a preferred response rate (less than or equal to 60 seconds) is satisfied when the temperature of the detection element is about 350° C. or more, and the response rate remains almost unchanged after a temperature around 600° C., from which it was found that the temperature of the detection element is preferably set to 350 to 600° C.

When the temperature of the detection element is 300 to 700° C., the applied voltage is preferably set to, for example, 0.68 V (with a spherical diameter of the detection element of 0.76 mm) to 1.85 V (with a spherical diameter of the detection element of 1.08 mm) (FIG. 8).

The reason that the top temperature shifted to a low temperature and the response rate decreased in the case where the diffusion limiting cap 34 was used is presumably because the gas was trapped in the cap. Also, from the results shown in FIGS. 18 and 19, it is considered that, when the temperature of the detection element is 300° C. or less, the conversion of the detection target gas is unlikely to advance, and, when the temperature of the detection element is as high as 700° C. or more, the reaction that converts NO to $N_2O_2$ is unlikely to advance.

Example 10

Figure 20:
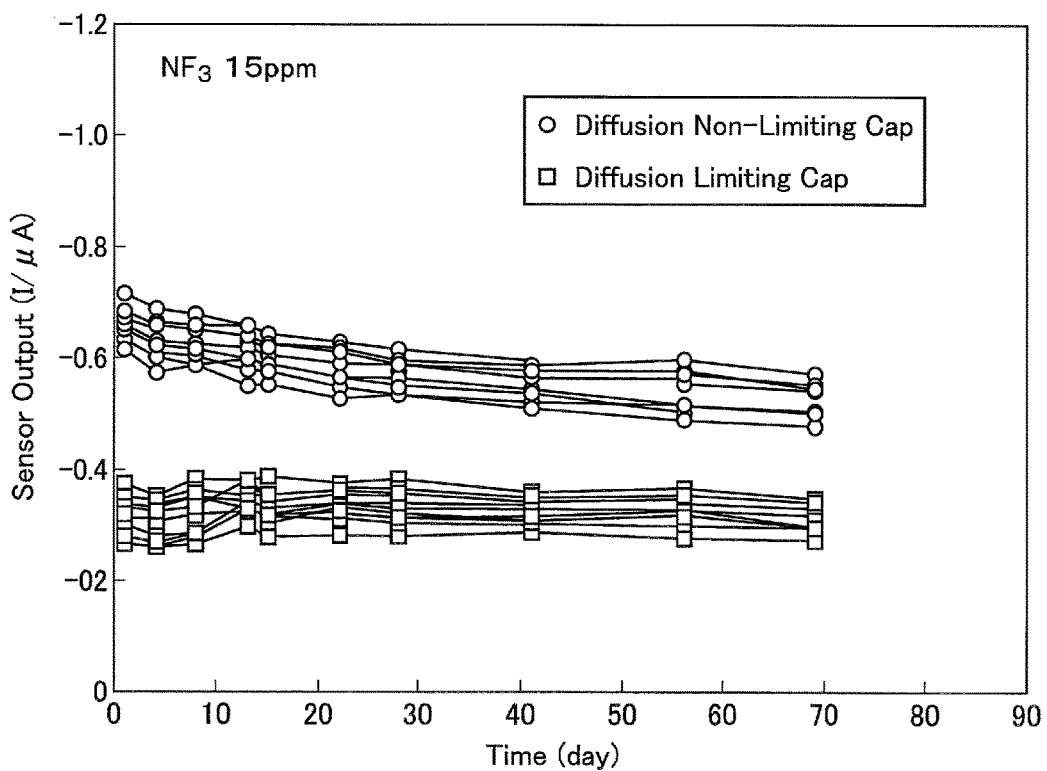
FIG. 20 is a graph showing the results of the stability of the detection element of the contact combustion-type sensor over time when two types of caps are used.

In the case where a contact combustion-type sensor was used as the heated catalyst portion 30A, the stability of the detection element over time was checked by using a diffusion non-limiting cap 33 (FIGS. 10 and 11) and a diffusion limiting cap 34 (FIGS. 12 and 13) as the cap used in the contact combustion-type sensor. Nitrogen trifluoride at a concentration of 15 ppm was used as the gas. The results are shown in FIG. 20.

As a result, after about two or more months of use, in the sensor in which the diffusion non-limiting cap 33 was used, degradation had advanced moderately, whereas in the sensor in which the diffusion limiting cap 34 was used, almost no degradation was observed.

In a sensor in which the diffusion non-limiting cap 33 is used, degradation advances moderately over time, but the sensor output is high, from which it can be considered that the sensor can be used sufficiently in locations where it will be used for a short period of time. On the other hand, in the sensor in which the diffusion limiting cap 34 is used, although the sensor output is low, the sensor output is stable over time, from which it can be considered that the sensor is suitable for use in locations where it will be used for a long period of time, such as a factory.

Example 11

In the examples given above, a configuration was used in which the heated catalyst portion 30A and the sensor element portion 30B were provided spaced apart from each other in the conversion portion 30, but the present invention is not limited thereto. The heated catalyst portion 30A and the sensor element portion 30B may be combined together and provided in the conversion portion 30.

For example, a configuration as shown in FIGS. 21 to 26 is possible in which a first sensor case 40 that constitutes the heated catalyst portion 30A and a second sensor case 50 that constitutes the sensor element portion 30B are combined together using bolts or the like.

Figure 21:
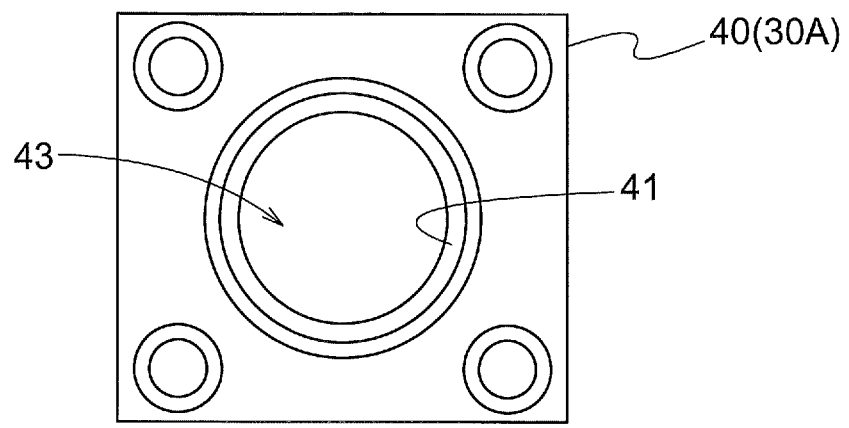
FIG. 21 is a schematic view of a first sensor case that constitutes a heated catalyst portion (as viewed from above).
Figure 22:
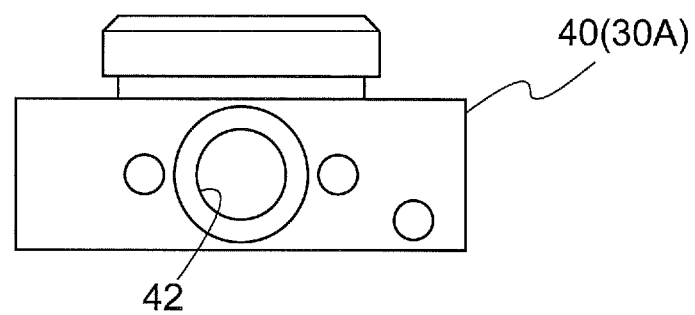
FIG. 22 is a schematic view of the first sensor case that constitutes the heated catalyst portion (as viewed from a side).
Figure 23:
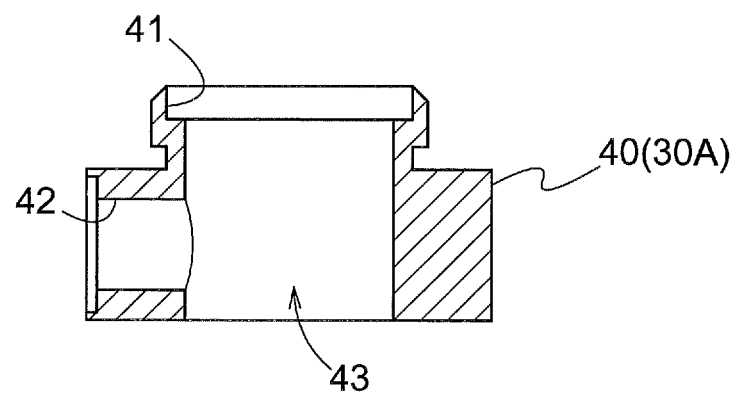
FIG. 23 is a schematic view of the first sensor case that constitutes the heated catalyst portion (cross-section).

The first sensor case 40 includes a first gas flow inlet 41 that allows a gas to flow into the first sensor case 40, and an insertion port 42 that allows a contact combustion-type sensor to be inserted, and a gas flow outlet 43 that allows the gas to flow out of the first sensor case 40 (FIGS. 21 to 23). The detection target gas enters through the gas flow inlet 41, and the conversion gas exits through the gas flow outlet 43.

Figure 24:
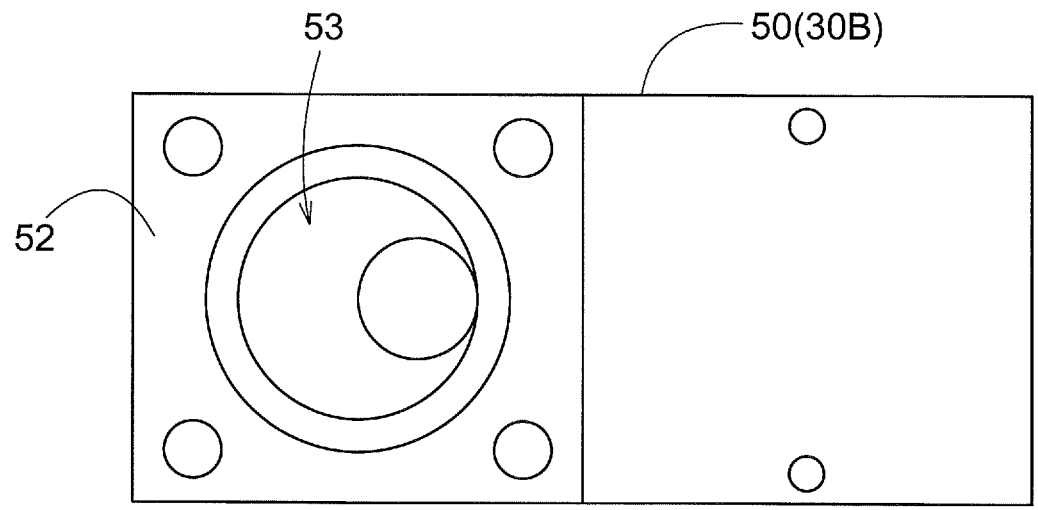
FIG. 24 is a schematic view of a second sensor case that constitutes a sensor element portion (as viewed from above).
Figure 25:
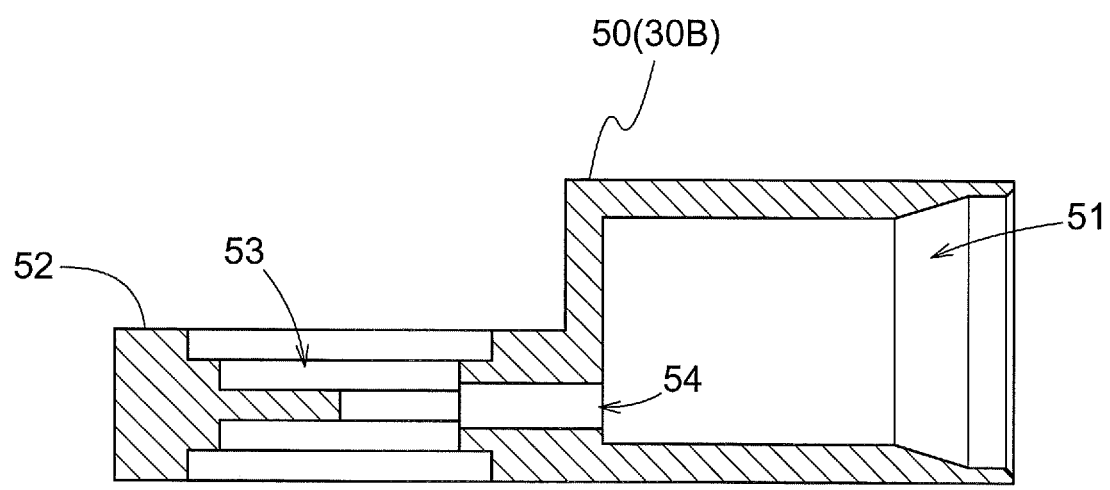
FIG. 25 is a schematic view of the second sensor case that constitutes the sensor element portion (cross-section).
Figure 26:
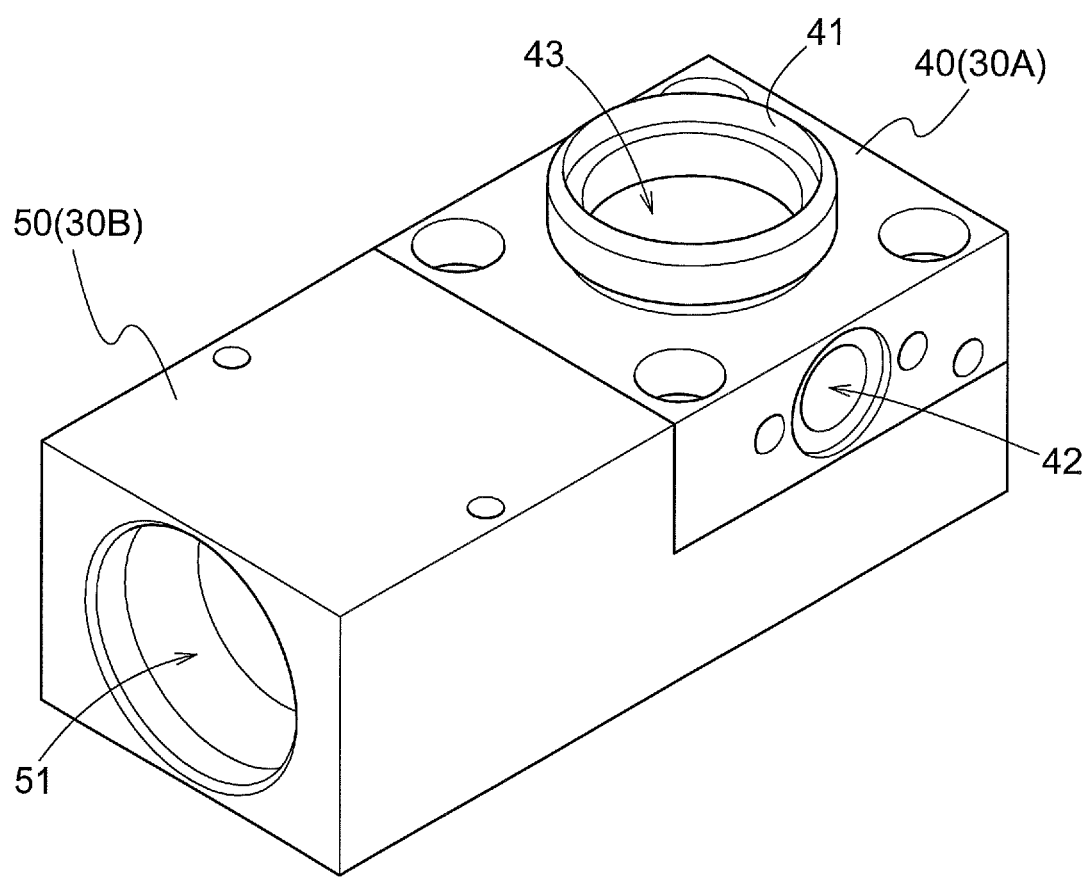
FIG. 26 is a schematic view of the first sensor case and the second sensor case when they are combined together.

The second sensor case 50 includes a sensor housing portion 51 that houses an electrochemical sensor or the like, and a mounting portion 52 on which the first sensor case 40 is mounted (FIGS. 24 and 25). Also, in the second sensor case 50, the mounting portion 52 includes a second gas flow inlet 53 that is connected to the gas flow outlet 43, and a communication portion 54 that allows the second gas flow inlet 53 to communicate with the sensor housing portion 51. With this configuration, the conversion gas that has flowed out from the gas flow outlet 43 flows into the sensor housing portion 51 via the second gas flow inlet 53 and the communication portion 54, as a result of which the conversion gas can be detected by the electrochemical sensor or the like.

As described above, with the configuration in which the heated catalyst portion 30A (the first sensor case 40) and the sensor element portion 30B (the second sensor case 50) are combined together, it is possible to reduce the capacity of the conversion portion 30.

Also, with a configuration in which the first sensor case 40 is not mounted on the second sensor case 50, it is possible to provide a configuration that includes only the sensor element portion 30B (the second sensor case 50), or in other words, a configuration that includes only an electrochemical sensor. It is thereby possible to easily select either a configuration that includes the heated catalyst portion 30A and the sensor element portion 30B or a configuration that includes only the sensor element portion 30B.

INDUSTRIAL APPLICABILITY

The present invention is applicable to a catalytic conversion-type sensor that detects a detection target gas by detecting a conversion gas produced through a reaction.

DESCRIPTION OF REFERENCE SIGNS

X: Catalytic Conversion-Type Sensor
10: Gas Flow Path
20: Diffusion Means
30: Conversion Portion
30A: Heated Catalyst Portion
30B: Sensor Element Portion
31: Catalyst

The invention claimed is:

1. A sensor that detects a detection target gas by detecting a conversion gas produced through a reaction, the sensor comprising:
   a gas flow path; and
   a conversion portion that is connected to the gas flow path, the conversion portion including:
      a diffusion means providing a partition between the gas flow path and the conversion portion, the diffusion means allowing the detection target gas to naturally diffuse;
      a catalyst portion comprising a catalyst, the catalyst portion configured to produce the conversion gas by causing the detection target gas to come into contact with the catalyst; and
      a sensor element portion comprising a sensor capable of detecting the conversion gas produced through the reaction, wherein
   the diffusion means is a resin film with a hole portion having a predetermined hole diameter.

2. The sensor according to claim 1, wherein the diffusion means has an air resistance of 800 mmPa·Pa$^{-1}$·s$^{-1}$ or less.

3. The sensor according to claim 1, wherein the diffusion means includes a gas permeable porous film provided adjacently to the resin film.

4. The sensor according to claim 1, wherein the reaction is oxidation.

5. The sensor according to claim 4,
   wherein the detection target gas is nitrogen trifluoride, and the conversion gas is nitrogen dioxide.

6. The sensor according to claim 5,
wherein the catalyst in the catalyst portion is a noble metal catalyst that contains Pd and Pt, and
the sensor element portion includes is an electrochemical nitrogen oxide sensor element that contains a noble metal carrying carbon and is configured to be capable of detecting nitrogen dioxide.

7. The sensor according to claim 1,
wherein the catalyst portion is a contact combustion-type sensor, and
a detection element included in the sensor has a spherical diameter of 0.76 to 1.08 mm, the detection element including the catalyst and being configured to respond to the detection target gas.

8. The sensor according to claim 1, wherein the catalyst portion is heated to 300 to 700° C.

9. The sensor according to claim 8, wherein the catalyst portion has an applied voltage of 0.68 to 1.85 V.

10. The sensor according to claim 1, wherein the reaction is thermal decomposition.

11. The sensor according to claim 10, wherein the diffusion means includes at least a gas permeable porous film.

12. The sensor according to claim 10,
wherein the detection target gas is hexafluoro-1,3-butadiene, and
the conversion gas is hydrogen fluoride.

13. The sensor according to claim 12,
wherein the catalyst in the catalyst portion is a noble metal catalyst that contains Pd and Pt, and
the sensor element portion is an electrochemical sensor element that contains a noble metal carrying carbon and is configured to be capable of detecting hydrogen fluoride.

14. A sensor that detects a detection target gas by detecting a conversion gas produced through a reaction, the sensor comprising:
a conversion portion that is connected to a gas flow path, the conversion portion including:
a diffusion means providing a partition between the gas flow path and the conversion portion, the diffusion means allowing the detection target gas to naturally diffuse;
a catalyst portion comprising a catalyst, the catalyst portion configured to produce the conversion gas by causing the detection target gas to come into contact with the catalyst; and
a sensor element portion comprising a sensor capable of detecting the conversion gas produced through the reaction, wherein
the diffusion means is a resin film with a hole portion having a predetermined hole diameter.

\* \* \* \* \*